(12) United States Patent
Pogue et al.

(10) Patent No.: US 11,633,145 B2
(45) Date of Patent: Apr. 25, 2023

(54) SPECIMEN IMAGING WITH X-RAY AND OPTICAL MEASUREMENT

(71) Applicant: THE TRUSTEES OF DARTMOUTH COLLEGE, Hanover, NH (US)

(72) Inventors: Brian Pogue, Hanover, NH (US); Samuel Streeter, Encampment, WY (US); Benjamin Maloney, Princeton, MA (US); Keith Paulsen, Hanover, NH (US)

(73) Assignee: THE TRUSTEES OF DARTMOUTH COLLEGE, Hanover, NH (US)

( * ) Notice: Subject to any disclaimer, the term of this patent is extended or adjusted under 35 U.S.C. 154(b) by 254 days.

(21) Appl. No.: 17/076,788

(22) Filed: Oct. 21, 2020

(65) Prior Publication Data

US 2021/0113146 A1 Apr. 22, 2021

Related U.S. Application Data

(60) Provisional application No. 62/923,673, filed on Oct. 21, 2019.

(51) Int. Cl.
*A61B 5/00* (2006.01)
*G06N 20/00* (2019.01)
(Continued)

(52) U.S. Cl.
CPC ............ *A61B 5/4312* (2013.01); *A61B 6/032* (2013.01); *A61B 6/502* (2013.01); *G06N 20/00* (2019.01);
(Continued)

(58) Field of Classification Search
CPC ......... G06T 7/0012; G06T 7/30; G06T 9/002; G06T 2207/10024; G06T 2207/10081;
(Continued)

(56) References Cited

U.S. PATENT DOCUMENTS

2010/0092064 A1* 4/2010 Li ............................ G16H 50/30
382/133
2011/0274338 A1* 11/2011 Park ....................... G06T 7/0012
382/133
(Continued)

OTHER PUBLICATIONS

Maloney et al., Structured light imaging for breast-conserving surgery, part I: optical scatter and color analysis, Journal of Biomedical Optics, vol. 24(9), Sep. 2019, pp. 8.
(Continued)

*Primary Examiner* — Irakli Kiknadze
(74) *Attorney, Agent, or Firm* — Cozen O'Connor

(57) ABSTRACT

A surgical specimen imaging system includes a micro-X-ray computed tomography (CT) unit for CT imaging of the specimen and a structured light imaging (SLI) unit for optical imaging at multiple wavelengths, multiple phase offsets, and multiple structured-light pattern periods including unstructured light. The system's image processing unit receives CT and optical images and is configured by firmware in memory to co-register the images and process the optical images to determine texture at multiple subimages of the optical images, determined textures forming a texture map. The texture map is processed by a machine-learning-based classifier to determine a tissue type map of the specimen, and the tissue type map is processed with the CT images to give a 3D tissue-type map. In embodiments, the firmware extracts optical properties including scattering and absorption at multiple wavelengths and the classifier also uses these properties in generating the tissue type map.

13 Claims, 13 Drawing Sheets

(51) Int. Cl.
*G06T 7/00* (2017.01)
*A61B 6/00* (2006.01)
*A61B 6/03* (2006.01)

(52) U.S. Cl.
CPC .................. *G06T 7/0012* (2013.01); *G06T 2207/10081* (2013.01); *G06T 2207/30068* (2013.01)

(58) Field of Classification Search
CPC ............. G06T 2207/30068; G06T 7/11; G06T 7/143; G06T 7/97; G06T 2207/30081; G06T 2207/20084; G06T 2207/20128; G06T 2207/30004; G06T 7/20; G06T 7/0016; G06T 17/00; G06T 2210/41; G06T 19/00; G06T 2207/10088; G06T 1/60; H04N 19/176; H04N 19/96; H04N 19/52; G06N 20/00; G06N 20/10; G06N 3/08; G06N 30/40; A61B 5/0075; A61B 6/032; A61B 6/502; A61B 5/4312; A61B 5/7267; A61B 5/0035; A61B 6/5294; A61B 5/742; A61B 5/7275; A61B 5/055; A61B 5/7264; A61B 5/0261; A61B 5/026; A61B 5/0263; A61B 8/06; A61B 6/504; A61B 6/507; A61B 5/7282; A61B 6/5217; A61B 10/0233; A61B 5/4887; A61B 5/7425; A61B 90/37; A61B 2010/0208; A61B 5/0059; A61B 5/0507; A61B 5/4088; A61B 5/441; A61B 5/165; A61B 5/1128; A61B 5/0022; A61B 3/14; A61B 5/0066; A61B 5/1176; A61B 1/01; A61B 1/00194; A61B 1/0005; A61B 1/000096; A61B 1/31; A61B 8/08205; A61B 6/5022; A61B 10/0041; A61B 5/0091; A61B 8/5223; A61B 8/085; A61B 6/037; A61B 6/03; A61B 6/0492; A61B 8/0833; A61B 6/5247; A61B 8/4209; A61B 8/5238; A61B 5/0095; A61B 8/0825; A61B 1/0052; A61B 8/485; A61B 8/406; G01N 23/046; G01N 2223/423; G01N 2223/6126; G06V 30/194; G06V 2201/031; G06V 10/40; G06V 10/774; G06V 30/36; G06V 40/1371; G06K 9/6256; G06K 9/6267; G16H 50/30; G16H 50/50; G16H 10/60; G16H 50/20; G16H 30/40; A61F 9/00821; A61F 9/00825
USPC .......................... 378/4, 19, 62, 63
See application file for complete search history.

(56) References Cited

U.S. PATENT DOCUMENTS

2018/0270474 A1* 9/2018 Liu .................. A61B 6/508
2020/0035350 A1* 1/2020 Sullivan ............... G06T 7/0014
2020/0066405 A1* 2/2020 Peyman ............. G06V 40/1365
2021/0249118 A1* 8/2021 Papagiannakis ....... G16H 50/20

OTHER PUBLICATIONS

Streeter et al., Structured light imaging for breast-conserving surgery, part II: texture analysis and classification, Journal of Biomedical Optics, vol. 24(9), Sep. 2019, pp. 12.

McClatchy III et al, Calibration and analysis of a multimodal micro-CT and structured light imaging system for the evaluation of excised breast tissue, Institute of Physics and Engineering in Medicine, Phys. Med. Biol. 62, Nov. 2017, pp. 19.

\* cited by examiner

Fig. 8. Summary of micro-CT performance metrics and size of minimum detectable objects (MDO) in the mammography target phantom.

| | SNR | Contrast | Exposure time (s) | Fiber$_{MDO}$ (mm diameter) | Specks$_{MDO}$ (mm diameter) | Masses$_{MDO}$ (mm thick) |
|---|---|---|---|---|---|---|
| 25 kVp | 23.8 | 1.81 | 144 | 0.54 | 0.24 | 0.25 |
| 50 kVp | 34.0 | 1.64 | 72 | 0.54 | 0.24 | 0.25 |

| Tissue subtype | Specimen (RoI) count | Sample count |
|---|---|---|
| Adipose | 26 | 56 |
| Connective | 6 | 20 |
| FCD | 5 | 24 |
| Intermediate-grade IDC | 5 | 14 |
| High-grade IDC | 8 | 29 |
| ILC | 6 | 20 |
| Total | 56 | 163 |

Fig. 10

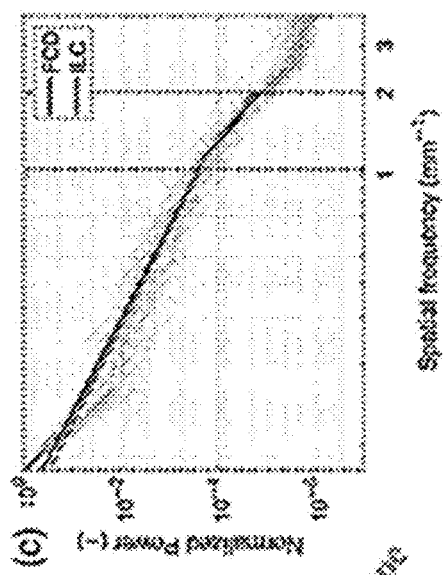 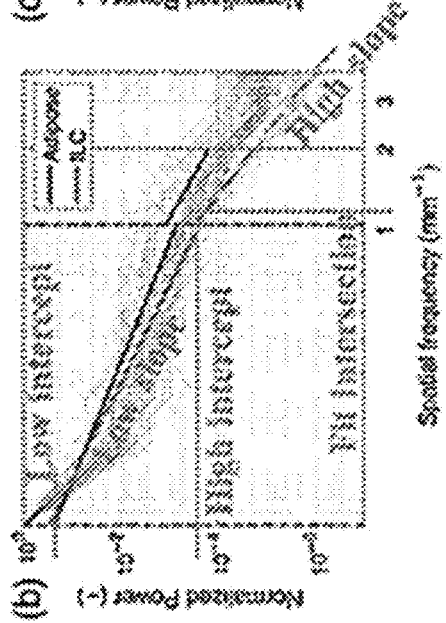 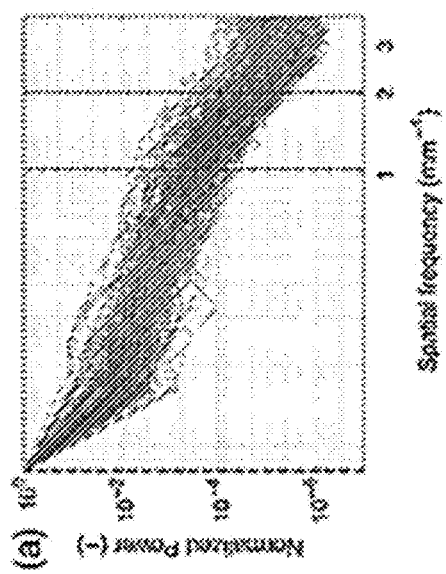
Fig. 12A  Fig. 12B  Fig. 12C
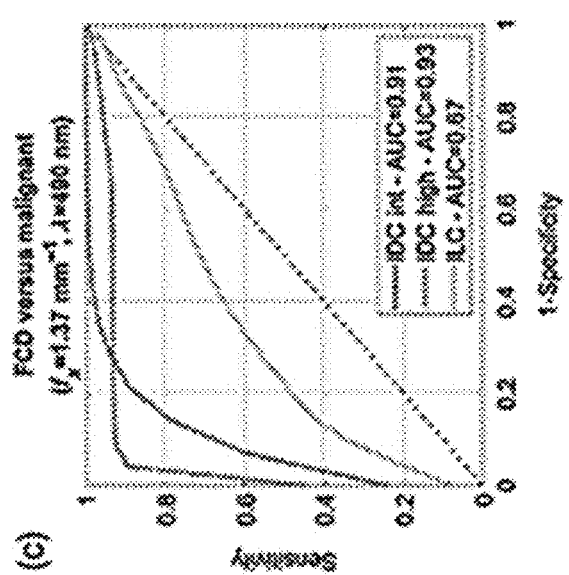 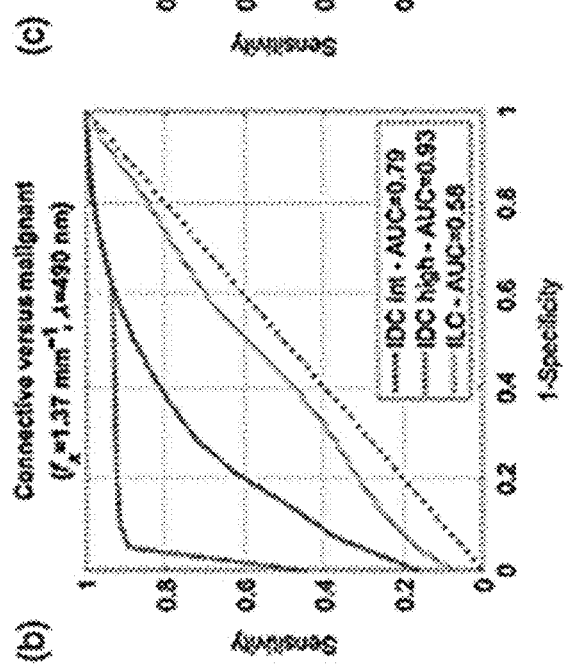 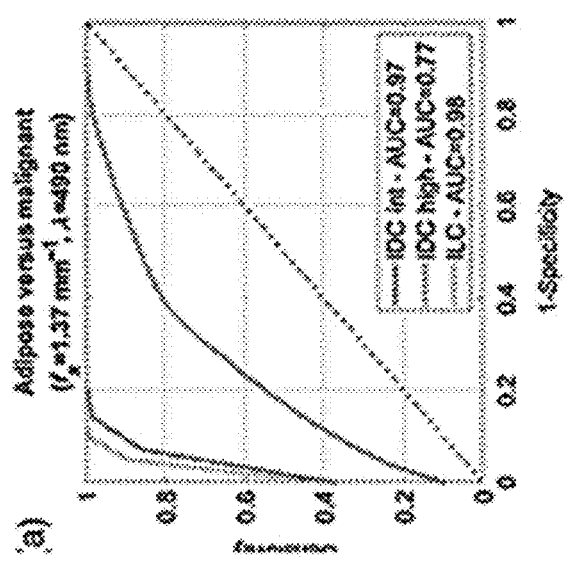
Fig. 14A  Fig. 14B  Fig. 14C Fig. 15
| | Adipose versus | | | Connective versus | | | FCD versus | | |
|---|---|---|---|---|---|---|---|---|---|
| | IDC int | IDC high | ILC | IDC int | IDC high | ILC | IDC int | IDC high | ILC |
| AUC | 0.97 | 0.77 | 0.98 | 0.79 | 0.93 | 0.58 | 0.91 | 0.93 | 0.67 |
| Sensitivity | 0.99 | 0.74 | 0.99 | 0.72 | 0.89 | 0.59 | 0.89 | 0.92 | 0.61 |
| Specificity | 0.86 | 0.67 | 0.90 | 0.71 | 0.95 | 0.50 | 0.79 | 0.92 | 0.65 |
| Accuracy | 0.92 | 0.70 | 0.95 | 0.72 | 0.92 | 0.55 | 0.84 | 0.92 | 0.63 |
| | (0.88 to 0.96) | (0.58 to 0.82) | (0.90 to 1.00) | (0.54 to 0.90) | (0.89 to 0.95) | (0.41 to 0.69) | (0.75 to 0.93) | (0.90 to 0.94) | (0.47 to 0.79) |
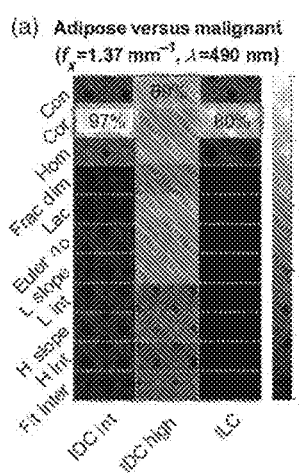
Fig. 16A
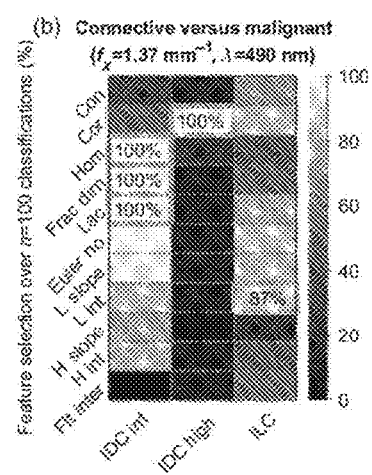
Fig. 16B
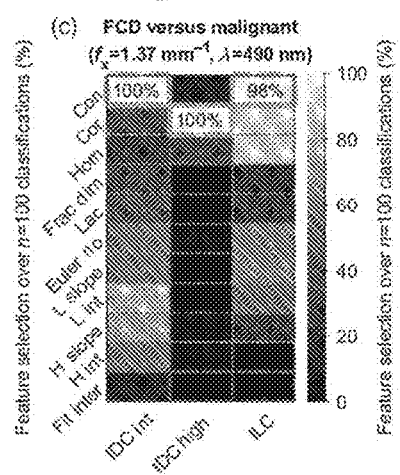
Fig. 16C System Data Flow Diagram

SPECIMEN IMAGING WITH X-RAY AND OPTICAL MEASUREMENT

CLAIM TO PRIORITY

The present document claims priority to U.S. Provisional Patent Application 62/923,673 filed 21 Oct. 2019. The entire contents of the aforementioned provisional patent application are incorporated herein by reference.

GOVERNMENT RIGHTS

This invention was made with government support under grant no. R01CA192803 awarded by the National Institutes of Health. The government has certain rights in the invention.

BACKGROUND

Breast-conserving surgery (BCS) in combination with radiation therapy is the most common treatment for stage I and II breast cancer. For BCS to be effective, excised tissue margins must be clear of malignancy (i.e., negative margins). However, 15% to 35% of BCS patients require a second surgery due to incomplete initial excision (i.e., one or more positive margins of the excised surgical specimen) as determined by postsurgical histopathological analysis. Typically, histopathological analysis is done visually by pathology technicians and pathologists performing labor-intensive searches of tissue sections. Several techniques have been proposed for improved BCS margin assessment, but significant limitations associated with each approach have prevented their widespread adoption, among these techniques are electrical impedance; diffuse reflectance, and Raman spectroscopic point-sampling; touch-prep cytology; and frozen section pathology. These point-sampling methods lack a comprehensive and/or practical approach to wide field-of-view (FOV) detection and thus are inherently time-consuming. Touch-prep cytology and frozen section pathology are resource-intensive to process even a subsection of a BCS specimen and suffer slow turnaround times. Most techniques lack the speed and wide FOV required to intraoperatively interrogate an entire BCS surgical specimen lump.

Technology assessment studies often adopt broad tissue categories, such as normal versus malignant. This categorization lumps together healthy adipose and fibroglandular tissues with benign lesions, such as fibrocystic disease (FCD), although these tissue subtypes contain different cellular and subcellular structures. Malignant tissue subtypes, including invasive ductal carcinoma (IDC) of low, intermediate, and high grade and invasive lobular carcinoma (ILC), are all characterized by different densities of nuclei and mitochondria, and different types and organizations of cells. Nevertheless, these malignant tissue subtypes are also commonly lumped together into a single malignant tissue category. Studies that rely on broad tissue categorization complicate the tissue classification task and jeopardize clinical potential.

SUMMARY

A system for specimen imaging with combined x-ray and optical measurement includes a micro-X-ray computed tomography (CT) unit adapted to provide voxel-based CT images of the specimen; a structured light imaging (SLI) unit adapted to provide optical images obtained at a plurality of wavelengths, a plurality of structured light phases, and at a plurality of structured-light pattern periods; an image processing unit adapted to receive the CT images and the optical images. The image processing unit is configured by firmware in memory to demodulate the structured light images; register the CT and optical images; extract like-tissue volumes from the CT images to form a volume map; process the optical images to determine texture at a plurality of subimages of the optical images, the determined textures forming a texture map; use a first machine-learning-based classifier to determine a surface tissue type map of the specimen from the texture map; and use a second machine-learning-based classifier to determine a three-dimensional tissue-type map from the surface tissue type map and the extracted like-tissue volumes from the CT images.

In another embodiment, a method of analyzing surgical specimens includes Illuminating a surgical specimen with structured light from a structured-light illuminator; imaging the surgical specimen to provide optical images at a plurality of illumination wavelengths, a plurality of structured light phases, and a plurality of structured-light pattern periods; demodulating the structured light images; processing the optical images to determine texture at a plurality of subimages of the optical images, the determined textures forming a texture map; and classifying with a first machine-learning-based classifier to determine a surface tissue type map of the specimen from the texture map. In particular embodiments, the method continues with obtaining X-ray computed tomography (CT) images of the surgical specimen; registering the CT and optical images; extracting like-tissue volumes from the CT images to form a volume map; and classifying with a second machine-learning-based classifier to determine a three-dimensional tissue-type map from the surface tissue type map and the extracted like-tissue volumes from the CT images.

BRIEF DESCRIPTION OF THE DRAWINGS

FIG. 8 is a table illustrating performance of the micro CT when imaging the breast phantom.

FIG. 10 is a table illustrating information regarding regions of interest (ROIs) in a clinical study of 42 surgical specimens of breast tissue.

FIG. 12A-12C represent power spectral density (PSD) curves for various tissue types.

FIGS. 14A, 14B, and 14C illustrate classifier performance for the SVM classifier used in the clinical study.

FIG. 15 is a table illustrating classifier performance for different tissue types.

FIGS. 16A, 16B, and 16C illustrate performance of the classifier as it discriminates specific tissue types.

DETAILED DESCRIPTION

The problem of intraoperative breast tissue classification could be simplified by ensuring sensitivity to key benign and malignant breast tissue subtypes. In addition, biopsies are performed prior to BCS procedures, and using this a priori tissue information could improve tissue margin diagnostic accuracy by reducing the number of possible malignant tissue subtypes to consider during classification.

Figure 1:
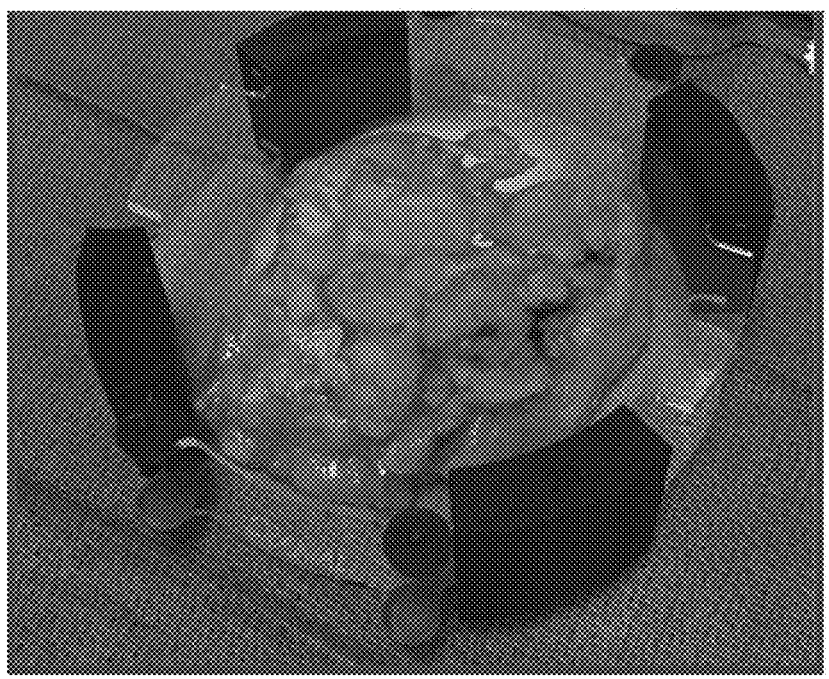
FIG. 1 shows tissue clamped in an acrylic holder between two optically clear plates.

Methods to combine data acquisition and image processing from a hybrid optical and x-ray imaging system are disclosed herein, for purposes of surgical specimen imaging to guide resection decisions. The goal is to optimally measure surface scattering structures from the optical scan and interior contrasting structures with the x-ray computed tomography image. The surface scan can be completed at high spatial frequency detection through line or multi-line illumination and imaging of the reflectance along these patterns of lines, both on the surface of the tissue as well as on the lateral sides of the tissue volume. A pair of optically clear plates (FIG. 2) are used to secure the tissue and flatten the surfaces as illustrated in FIG. 1 to allow for optical scanning, the sample is also x-ray computed tomography (CT) scanned laterally. Both optical scanning and CT scanning are done in the machine illustrated in the block diagram of FIG. 3. Movement of the specimen in the x-ray beam by rotation in the horizontal plane is used for computed tomography imaging, and this motion may also be used for simultaneous optical scanning of the surface. The plates have x-ray opaque fiducial marks to allow for marking of the clinical orientation of the specimen within the scan as well as for determining an orientation after the scan.

Figure 4:
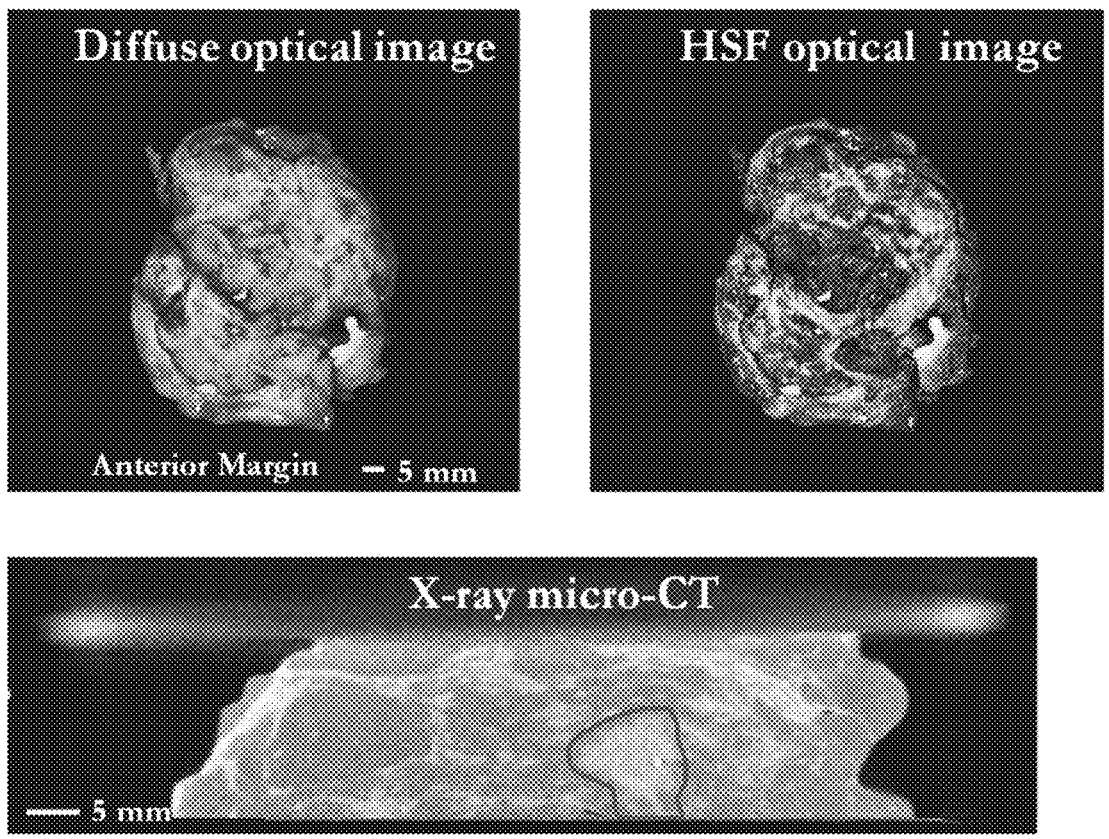
FIG. 4 illustrates a diffuse optical image, a high spatial frequency (HSF) structured-light optical image, and an X-ray micro-CT image.
Figure 5:
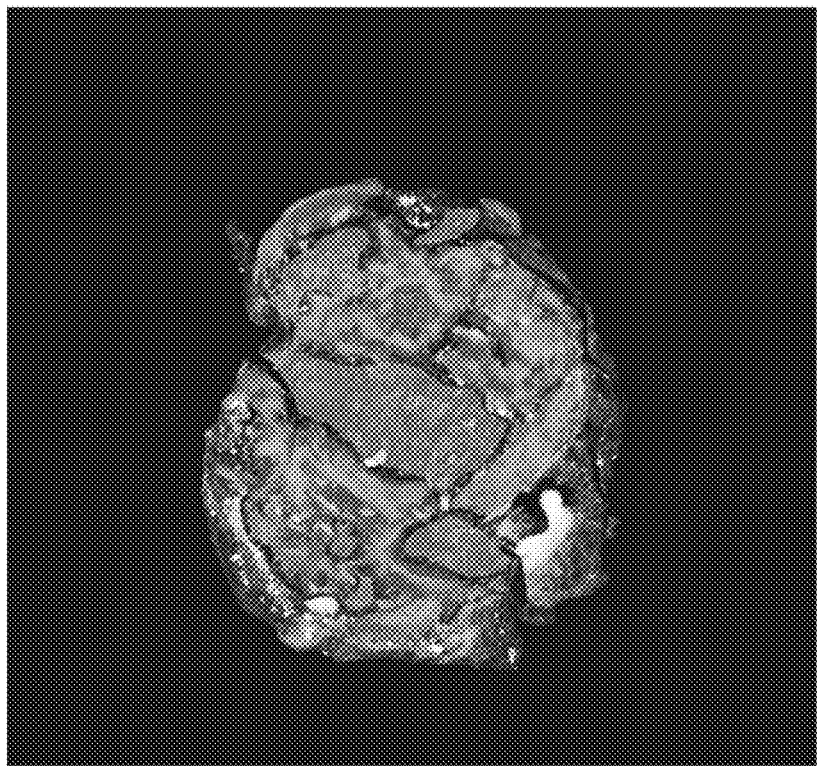
FIG. 5 illustrates a classifier-output tissue-type map image with particular tissue types highlighted.
Figure 6:
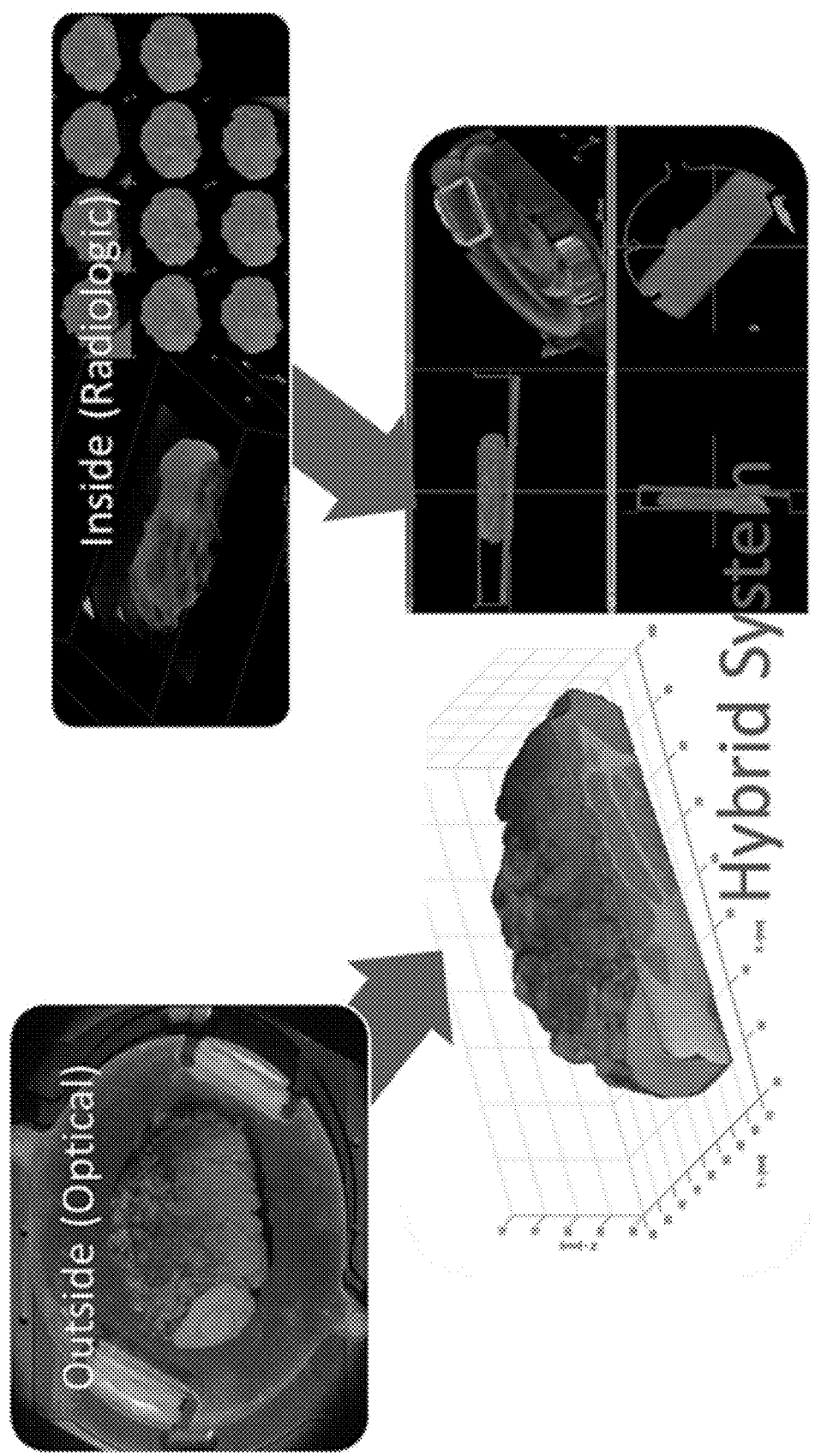
FIG. 6 shows one hybrid system with intraoperative margin detection for breast conserving surgery.

Methods to optimize the algorithm analysis of the data are disclosed. Following scanning, the optical surface data from diffuse optical imaging, from HSF structured-light imaging, and x-ray CT data may be displayed individually as illustrated in FIG. 4, and are combined to identify margins of surgical specimens that might have malignant tissue present, to assist in surgical decisions. In embodiments, a trainable machine-learning-based classifier is used to classify tissue types to produce a classifier image as illustrated in FIG. 5. The classifier image is based on the HSF structured light image at the tissue surfaces, the CT images deep within the tissue, and a combination of the two where both methods provide significant information as illustrated in the composite FIG. 6.

In embodiments, the detection of malignancy may be informed by using information about the patient and the prior biopsy diagnosis in the classifier to maximize the accuracy and efficiency of the detection algorithm. Additionally, the interior volumetric or exterior surface x-ray CT data are used to identify regions of the specimen which might need more optical imaging or analysis such as areas with higher than normal chances of detection of suspected malignancy on the exterior surgical specimen margin. Alternatively, the optical scan data may be used to inform the x ray CT data for refined approaches to segmentation or analysis of the image data.

High spatial frequency (HSF) structured light imaging (SLI), has shown label free sensitivity to changes in freshly resected breast morphology over a large field of view (FOV). This approach, originally termed spatial frequency domain imaging (SFDI), has advantage of structured illumination's ability to tune depth sensitivity with the spatial modulation frequency. While the contrast at low spatial frequencies is dictated by absorption features (presence of blood, fat) and diffuse scattering (density of tissue), the contrast of sub-diffusive high spatial frequency images is dictated by both scattering intensity and the angular distribution of scattering events, or phase function, as photon propagation is constrained to superficial volumes with minimal volumetric averaging over tortuous photon path-lengths. The phase function arises from the underlying physical properties of tissue ultrastructure. Recent studies have used sub-diffusive structured light imaging to quantify angular scattering distributions through the phase function parameter $\gamma$, which is related to the size-scale distribution of scattering features. This phase function parameter $\gamma$, along with the reduced scattering coefficient $\mu'_s$, has been used to cluster benign and malignant breast tissue pathologies in freshly resected human breast specimens and morphologies within murine tumors, as different tissue morphologies with unique densities and size-scale fluctuations manifest unique light scattering properties.

Although SLI can generate wide-field images of the specimen surface, it is unable to provide high resolution (<1 mm) depth contrast or a tomographic reconstruction through the specimen volume. Micro-computed tomography (CT) is a promising technique for intraoperative visualization of breast specimens, which can be manufactured in a shelf shielded, mobile form. factor. By reconstructing x-ray absorption in three dimensions (3D) thereby resolving overlaying features, micro-CT increases low contrast resolution relative to x-ray projection imaging, and thus, yields a more accurate delineation of the tumor core extent and proximity to the margin in surgical breast specimens. Furthermore, micro-CT and SLI can be symbiotic as the former inherently loses image quality at the tissue-air interface, where the latter becomes the most sensitive at the tissue-air interface.

Figure 2:
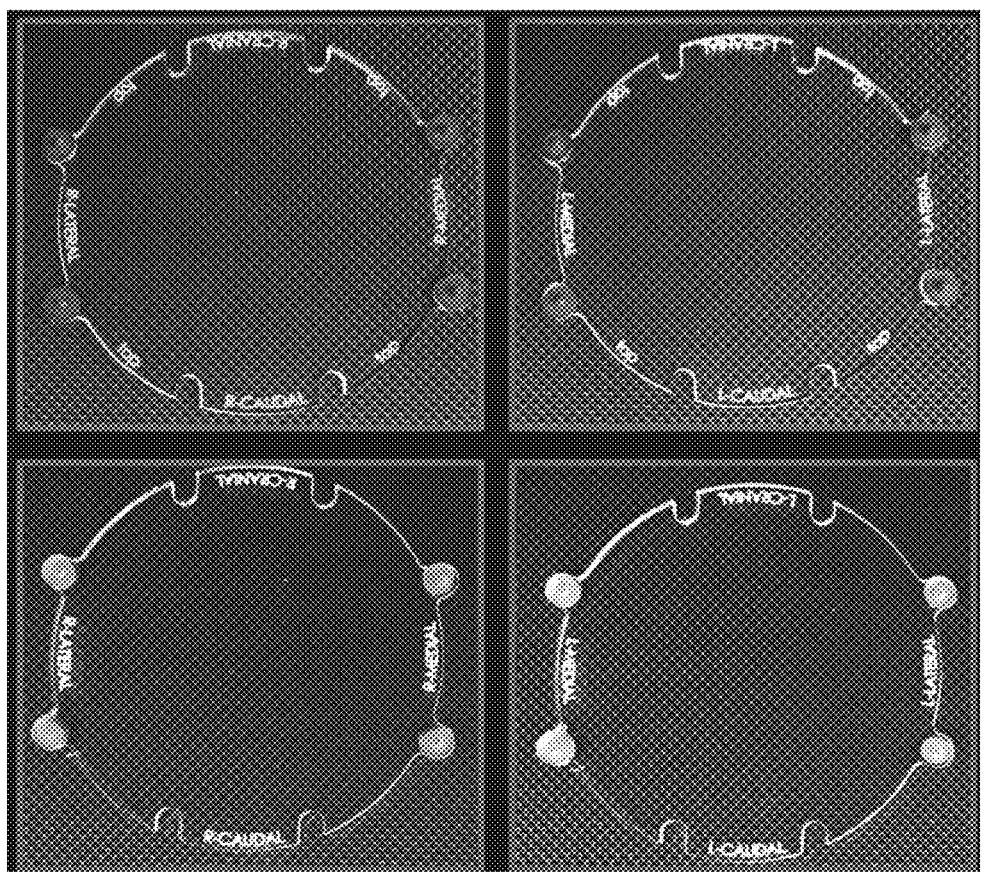
FIG. 2 shows optically clear plates with fiducial markers dedicated for maintaining the anatomical orientation of right breast specimens and left breast specimens.
Figure 3:
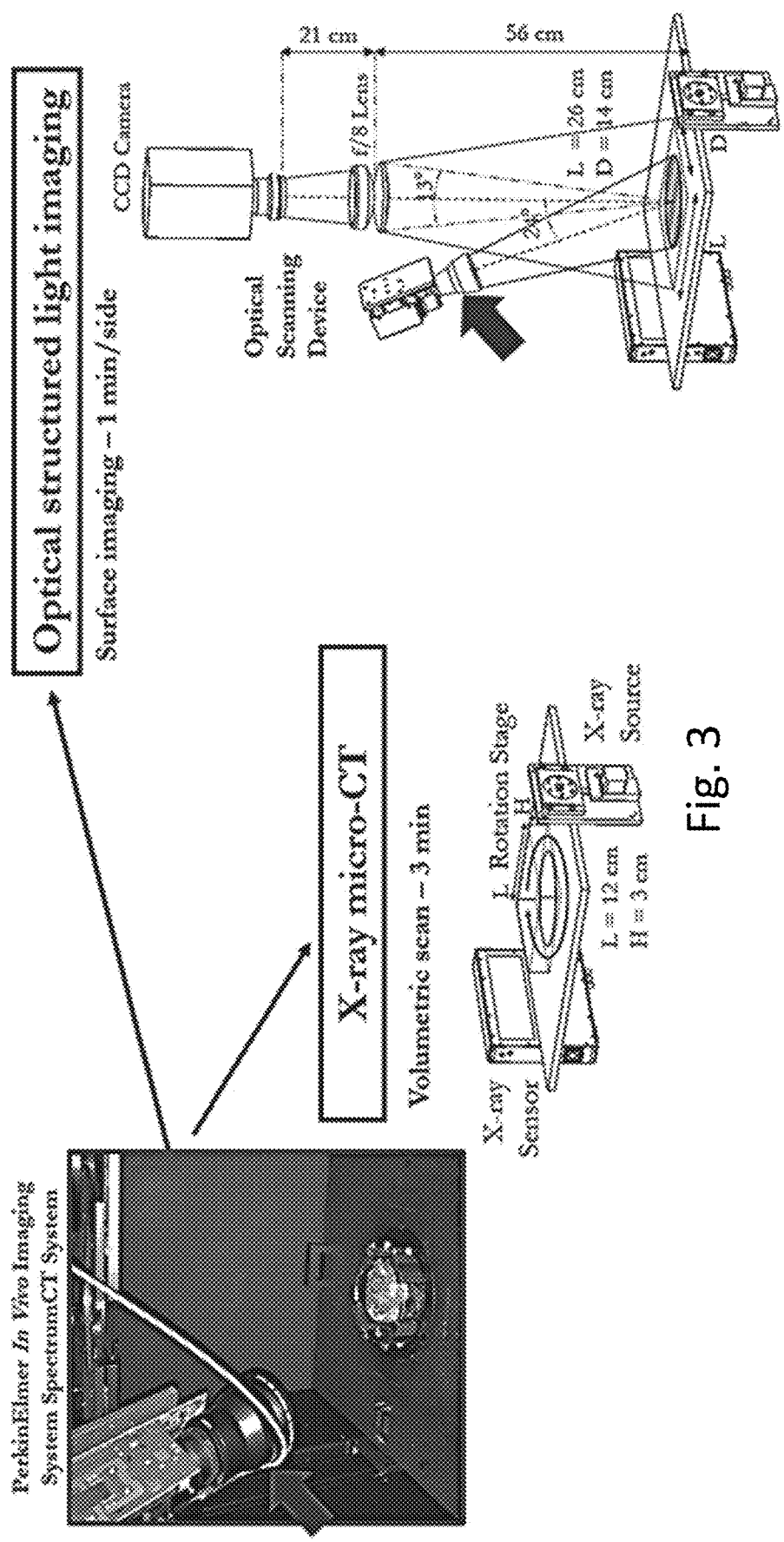
FIG. 3 shows the Perkin Elmer In Vivo Imaging System (IVIS) Spectrum CT System providing X-ray micro-CT and Optical structured light imaging.
Figure 7:
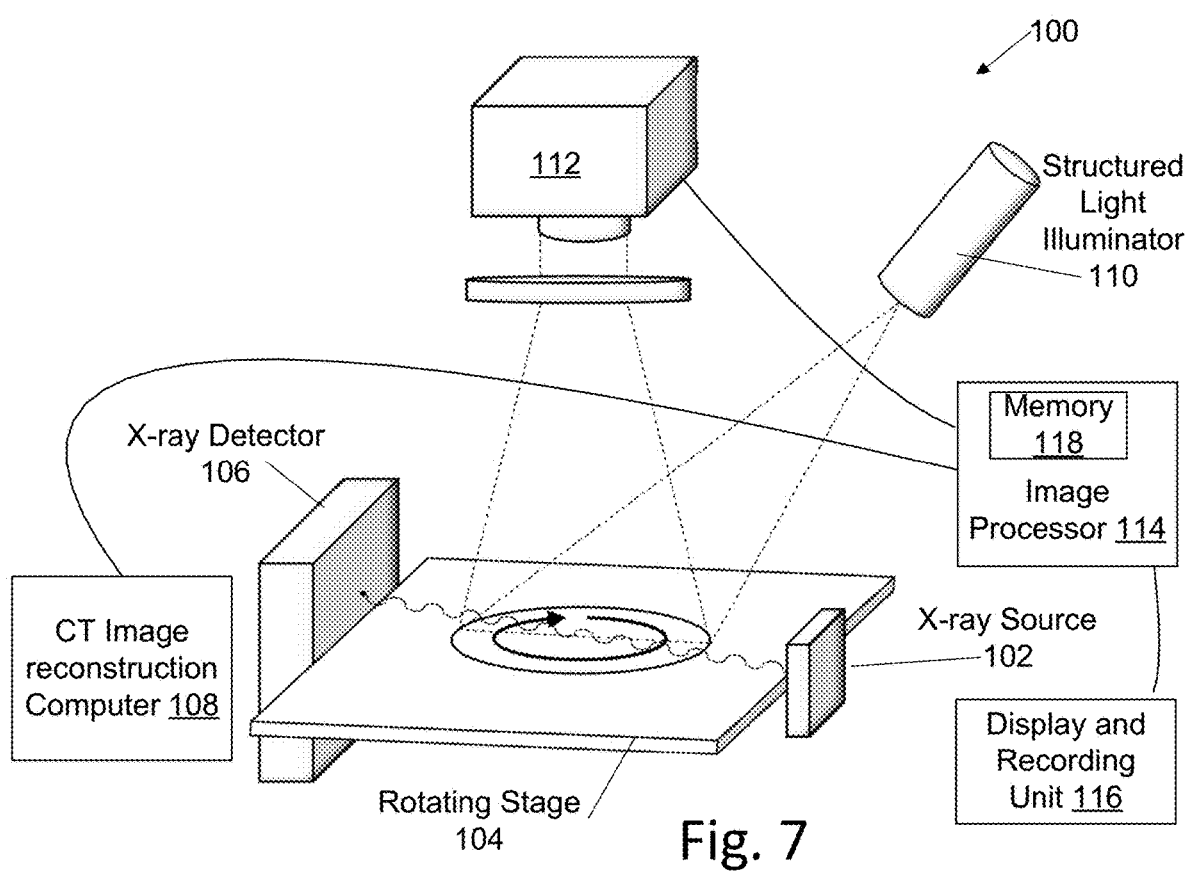
FIG. 7 shows a schematic illustrating the core concept of synchronous micro-computed tomography scanning and structured optical imaging via a rotating stage.

Our system is a multimodal imaging system 100 as illustrated in FIG. 7, combining volumetric micro-CT and superficial SLI. The system includes an X-ray source 102, a rotating stage 104 upon which the flattened surgical specimen clamped between the clear plates of FIG. 2 is placed, and an X-ray detector 106. A CT image reconstruction computer 108 is provided to reconstruct CT images from signals from X-ray detector 106. An optical system including a structured-light illuminator 110 is provided to illuminate tissue (not shown) on rotating stage 104 so that it may be imaged with an optical camera 112. Tomographic slice images from the CT image reconstruction computer 108 are fed to an image processor 114 along with optical images from optical camera 112, images are co-registered, analyzed, and pixels or voxels classified as to tissue type in image processor 114; resulting images including CT images, HFT-SLI images, composite images, and classified images are provided by image processor 114 to a display and recording unit 116 where they may be viewed by a surgeon. Image processor 114 is configured to process and classify images by firmware 118.

This multimodal imaging system 100 is provided for evaluation of excised breast tissues and other surgical specimens. Accuracy of the optical property inversion method was validated on comprehensive sets of flat phantoms perpendicular to the imaging plane. As an exemplary embodiment, ex-vivo breast specimens were imaged during gross examination, yielding visualization of the tumor extent in three dimensions (3D) with co-registered structured light images and scatter parameter maps as well as CT images.

Exemplary Multimodal Micro-CT with Multi-Spectral SLI System

The prototype multimodal SLI/micro-CT system was created from a modified and re-purposed IVIS Spectrum CT, which is a pre-clinical bioluminescence imaging and micro-CT system (PerkinElmer Inc., Hopkington, Mass.), which provides the X-ray source 102, detector 106, rotating stage 104, and CT image reconstruction computer 108. The HFT-SLI addition included the native IVIS system's charged coupled device (CCD) camera 112 (Andor iKon, Andor Technologies Ltd., Belfast, UK) and a retrofitted digital light projector (DLP) (CEL5500 Fiber, Digital Light Innovations Inc., Austin, Tex.) with a 3.6× telephoto lens as a structured light illuminator 110. Due to size constraints within the imaging cabinet, the DLP is rotated 22° with respect to the CCD. Light was delivered through an optical fiber to the DLP, was focused onto the digital mirror device (DMD) creating the structured light patterns. and was then focused on the specimen to illuminate the specimen with the pattern. The DLP was connected to an external virtual monitor which controls the illumination pattern at a frame rate of 60 Hz. The illumination source was a supercontinuum laser (SuperK Blue, NKT Photonics, Denmark) with a tunable line filter (SuperK Varia, NKT Photonics, Denmark) to select the wavelength band. At the shelf stage height used for imaging, the diameter of the circular illumination field of the DLP was 14 cm with a projection resolution of 168 lines/cm, while the imaging field was 26 cm×26 cm with a sampling resolution of 126 μm. Only a subset of the CCD corresponding to 13 cm×13 cm area covering the illumination field was read out to minimize acquisition time. The self-shielded micro-CT of the Perkin Elmer system was a cone-beam CT in a 'pancake' geometry, with the specimen rotating through 360° on rotating stage 104.

Data Acquisition and Processing

For the multimodal acquisition, micro-CT and SLI data were sequentially acquired with separate software packages. The specimen was placed on the rotation stage 104, and the micro-CT scan was acquired and reconstructed through the Perkin Elmer Living Image software. A 1 mA current was used and the tube peak kilovoltage (kVp) and exposure time were set to either 25 kVp and 200 ms/exposure or 50 kVp and 100 ms/exposure, yielding 2.4 min and 1.2 min total scan times for the low and high energy settings, respectively.

The filtered back-projection reconstruction time was about 2 min for a reconstructed FOV of 12 cm×12 cm×3 cm with 150-micron cubic voxels.

After the micro-CT scan was completed, an SLI acquisition occurred with a custom LabView routine (National Instruments, Inc., Austin, Tex.). For all scans in our study, seven wavelengths were acquired, λ=[490, 550, 600, 650, 700, 750, 800] nm, with a 15-nm bandwidth, and at each wavelength, 18 one-dimensional sinusoidal projections were recorded at 6 spatial frequencies, fx=[0.05, 0.15, 0.61, 0.78, 0.92, 1.37] mm$^{-1}$ with 3 phase offsets, ct.=[0, 120, 240]°. In this protocol only one rotation angle was considered to minimize the time of a SLI scan, which was about 8 min for both acquisition and saving. In our preliminary studies, after specimen scanning, an 8-in.×8 in. silicone titanium oxide (TiO2) phantom and a 10-in.×10 in. 99% reflectance standard (Labsphere, Inc., Sutton. N.H.) were imaged for calibration.

While 3 phase offsets seem sufficient for imaging, SLI imaging map be performed at more phase offsets such as four phase offsets at [0, 90, 180, 270]°; or in embodiments 5 or 6 distinct phase offsets.

SLI data processing was initially performed with scripts in MATLAB (2016a). Images were demodulated by $Id = \sqrt{2}/3 \cdot \sqrt{(I_{\theta 1} - I_{\theta 2})^2 + (I_{\theta 1} - I_{\theta 3})^2 + (I_{\theta 2} - I_{\theta 3})^2}$, where θ1, θ2, and θ3 are the three phase offsets for a given spatial frequency and wavelength. In other embodiments, firmware 118 is configured to perform demodulation. Due to minor fluctuations in laser power, phase images were scaled so that each had the same mean over the illuminated area to minimize demodulation artifacts. Also, a median filter with 3×3 pixel kernel was applied to demodulated images to remove noise and any specular reflections arising from minor fluctuations of the tissue surface profile. These specular reflections were mitigated by flattening the tissue surface between two transparent acrylic plates and using an oblique projection scheme. Optical property maps were calculated with a sub-diffusive model inversion method described previously (Kanick S, Krishnaswamy V, Gamm U, Sterenborg H, Robinson D, Amelink A and Pogue B, 2012 Scattering phase function spectrum makes reflectance spectrum measured from intralipid phantoms and tissue sensitive to the device detection geometry Biomed. Opt. Express 3 1086-100).

A non-linear least squares routine determined optical properties by minimizing the difference between measured calibrated reflectance and model-based predicted reflectance over all spatial frequencies and wavelengths where A, B are the scattering amplitude and power, respectively. The phase function parameter –γ was a free fit variable at each wavelength. For tissue specimens, the absorption coefficient, $\mu_a$, was assumed to be a linear sum of oxygenated hemoglobin, deoxygenated hemoglobin, and β-carotene with basis spectra obtained from the Oregon Laser Medical Center (OLMC) spectra database.

Color images were also reconstructed from the multispectral SLI data. For the 5 wave-lengths in the visible spectrum. λ=[490, 550, 600, 650, 700] nm, SLI images were trans-formed into a RGB color-space using the 1931 International Commission on Illumination (CIE) tristimulus values (Smith and Guild 1931). For each illumination band, the x,y,z chromaticity values were calculated and normalized, and multiplied by the demodulated intensity of the specimen and the 99% reflectance standard for each respective wavelength band. The resulting x, y, z image stack was converted to RGB space with the value of the 99% reflectance standard set to be the white point.

3D-2D Co-Registration and Visualization

Accurate calibration and co-registration of the 2D image coordinates to the 3D CT coordinates are needed for a multimodal visualization. Camera calibration with the optical system was performed to account for lens and perspective distortion. This was done using the Open Source Computer Vision Library (OpenCV) Camera Calibration and 3D Reconstruction Software (Open Source Computer Vision Library 2016). with which the intrinsic camera matrix and radial and tangential lens distortion coefficients were calculated. Images acquired were corrected using the undistortImage function in the MATLAB Computer Vision System Toolbox (version 2016a). The transformation matrix from the optical image coordinates to the CT coordinates in the XY plane was calculated using Procrustes alignment method. Because the optical and micro-CT systems were rigidly fixed, these calibrations were performed once, and were used in all imaging experiments reported here.

With the optical system calibrated, a module was created to co-register and display an acquired CT/optical scan automatically which was integrated into NIRFAST Slicer software (www.dartmouth.edub~nidnirfast/). A diagram of the data-processing and work-flow is shown in FIG. 2 for a hemispherical gelatin phantom. The height map was extracted from the CT volume by determining the most superficial CT voxel above a manual threshold, for each x, y vector of voxels. Next, the optical image was undistorted and then co-registered to CT coordinates through the linear transformation. Finally, for each point on the height map, the scalar value of the nearest optical data point was assigned. With this 3D scalar data, a triangular surface mesh was created in the Visualization Toolkit (VTK) file format, which was then simultaneously rendered with the CT volume in the Slicer environment.

Micro-CT, Optical, and Co-Registration Phantoms

To quantify image quality of the micro-CT system, a mammography target phantom (Mamma 156 Phantom, Gatnmex Inc., Middleton, Wis.) was utilized. This mammography accreditation phantom is composed of acrylic with a wax insert containing various fibers, hemispherical masses, and specs. It has been designed to simulate a compressed breast comprised of 50% glandular and 50% adipose tissue and size of 10.2 cm×10.8 cm×4.2 cm. While the phantom was larger than the micro-CT FOV, surgical specimens are smaller than the entire breast and contain less background tissue; thus, only the wax insert was imaged. Furthermore, if the entire phantom were imaged, partial volume artifacts would have greatly degraded image quality, with a large portion of phantom having been outside of the x-ray beam.

The spatial resolution of the SLI system was analyzed with a step phantom. A sheet of highly absorbing black paper was placed on a 99% reflectance standard creating a sharp edge between a highly reflective and nearly non-reflective surface. The spatial resolution was analyzed by characterizing the response of the imaging system across the edge.

To validate sensitivity of the SLI system and accuracy of the optical property inversion method, two sets of tissue simulating aqueous phantoms were imaged. In the first set of phantoms, the size-scale distributions of scatterers were varied by selectively titrating various concentrations of Intralipid (IL) and a solution of 140 nm polystyrene spheres. The optical properties of the sphere solution were calculated with Mie theory, while the optical properties of IL were taken from previous publications, and a discrete particle model was used to calculate the optical properties of different ratios of each solution. The various solutions contained $\gamma$ between 0.99 and 2.00, and $\gamma$ of each phantom was matched at $\lambda=650$ nun. In the second set of phantoms, absorption and scattering were varied independently with various concentrations of IL and whole porcine blood. The hemoglobin concentration of the blood was measured at 13.4 g/dl, and to maintain neutral pH, phosphate buffer was used for dilution. Solutions were made with [0.5, 1, 2]% IL and [0.5, 1, 2, 4]% blood volume fractions (BVF), yielding phantoms in the range $0.8\text{-}10^5$ over the acquired wavelength range assuming fully oxygenated blood. The influence of blood on the scattering properties were negligible compared to the influence of IL, based upon previous studies measuring the optical properties of blood. Each phantom set was imaged in a 24-well plate having black, non-transparent walls and each well had 2.5 ml of solution.

Accurate co-registration between the micro-CT and optical imaging system was experimentally validated and quantified with a custom-made phantom containing radio-opaque and optically bright markers. The markers were ⅛ in. acetal pins, the top surfaces of which were coated in commercial liquid paper to increase optical reflection. Two orthogonal lines of 7 markers with approximately 1 cm spacing were set on optically dark paper creating a cross-hair pattern. The co-registration accuracy was measured as the co-localization of the marker positions in the CT and SLI datasets.

Imaging a Surgically Resected Breast Specimen

To demonstrate the system acquiring and displaying a multimodal clinical dataset, a freshly resected breast tissue specimen was scanned. The imaging protocol did not interfere with standard of care posing minimal risk to the patient, and was approved by the Dartmouth Hitchcock Medical Center (DHMC) Internal Review Board (IRB) and the Committee for the Protection of Human Subjects (CPHS). After each breast surgery specimen was received by the Department of Pathology, it was 'bread loafed' and grossly assessed per standard of care. Cut tissue specimens with superficial lesions were imaged with system. To maintain the orientation of the specimen through imaging and provide a flat imaging surface, it was placed in a customized holder, consisting of two ⅛ in. thick, optically-clear acrylic plates, between which the specimen was secured with elastic bands. The silicone calibration phantom, having a refractive index similar to tissue, was likewise imaged with the acrylic plate. Immediately after imaging, each specimen was cut into cassette sized sections (~1 cm). photographed, and underwent standard histological processing of dehydration, fixation, wax embedding, sectioning and hematoxylin and eosin (H&E) staining. Resulting histology was evaluated by a trained pathologist and included in the patient's report.

Micro-CT Analysis of Mammography Target Phantom

The micro-CT target phantom analysis resulted in the same minimum detectable objects (MDO) for low and high kVp energy scans, with only the smallest fiber and smallest speck cluster not clearly visible. This yielded a limiting resolution of 240 pm for a high-contrast spherical object. To assess image quality of the micro-CT, the signal-to-noise ratio (SNR) and contrast were evaluated for each kVp scan. A single slice through the largest mass was analyzed, with the mean, p, and standard deviation, o, of the linear attenuation coefficient calculated in a region of interest (ROI) in both the largest mass and in the abutting background.

A tabulated summary of the metrics quantifying the micro-CT performance is shown in FIG. 8. Because of the shorter scan time, superior SNR, and similar contrast, subsequent micro-CT scans were acquired with the 50 kVp, 100 ms/exposure, scan settings.

Multi-Spectral Structured Light Imaging Analysis

Figure 9:
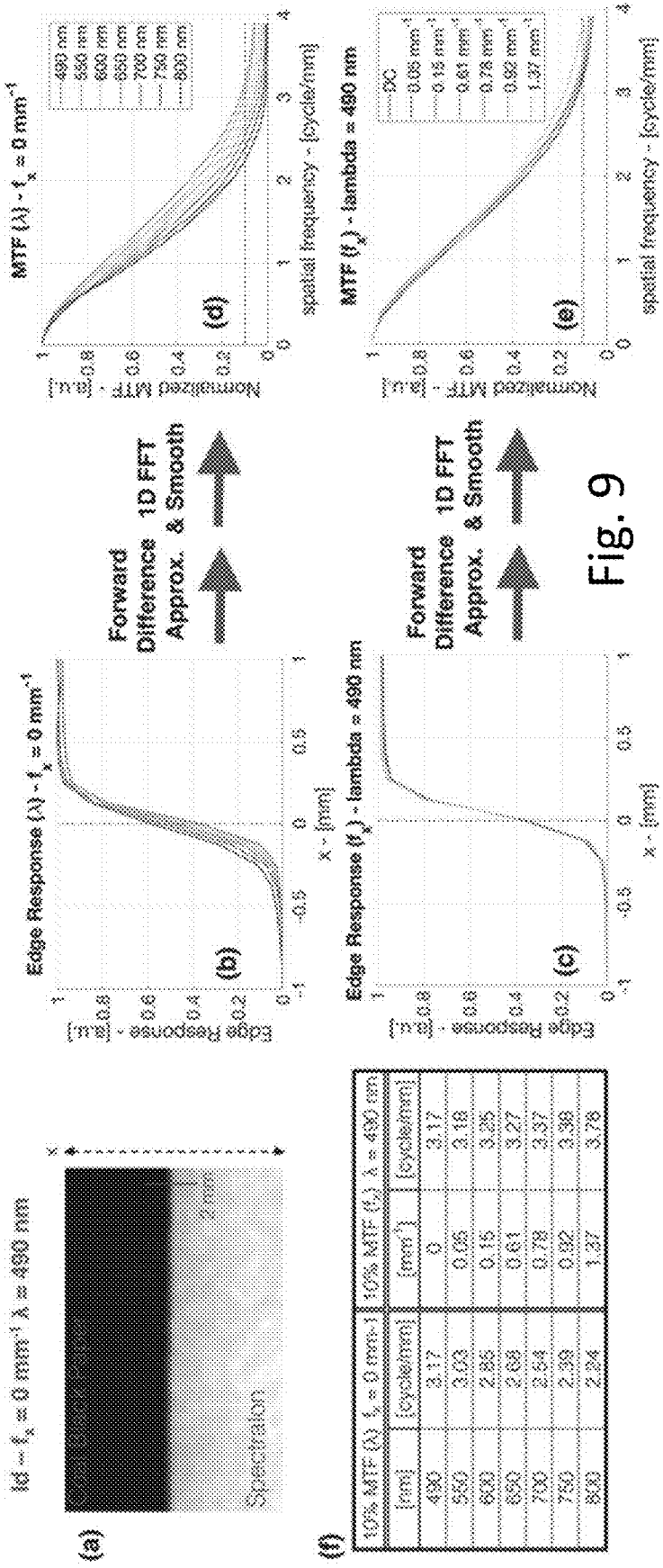
FIG. 9 is an illustration of edge responses and resolution of the system.

The spatial resolution of the demodulated intensity as a function of spatial frequency and wavelength was tested by analyzing the response of a step phantom. In FIG. 9 panel (a), a captured image of the step phantom is shown for A=0 mm-1 and A=490 nm. The direction of the illumination frequency is at a 68° angle with the step, while the y-axis of the CCD is parallel, so that the captured imaged can be averaged along the step. Measured edge responses across the step are shown for each imaged wavelength in FIG. 9 panel (b). A forward difference approximation and subsequently a fast Fourier transform (FFT) was applied to each edge response to calculate the corresponding modulation transfer functions (MTF), shown in FIG. 9 panel (c). Each MTF was normalized by its maximum value and smoothed with a 5-pixel moving average filter. Edge responses and MTFs are likewise shown in FIG. 9 panel (d) and (e) respectively, for each imaged spatial frequency at A=490 nm. The limiting spatial resolution is quantified as the point where the MTF reaches 10% of its maximum value. These values are tabulated for the variation in wavelength and spatial frequency. For the case of diffuse illumination, a clear trend of increasing spatial resolution from 2.24 cycles mm-1 to 3.17 cycles mm-1, occurs as wavelength decreases from 800 nm to 490 nm. Although the reflectance standard is near completely reflective, this wavelength dependent behavior is still expected as the lower edge of the phantom will have a higher scattering cross section with shorter wavelength light, and therefore, a shorter transport length resulting in a sharper response. Also, as the spatial illumination frequency increases, a slight increase is found in spatial resolution, which is also expected as increasing the spatial illumination frequency constrains the light transport to become more superficial and localized, also resulting in a sharper response. Results revealed a maximum spatial resolution of 3.78 cycles $mm^{-1}$ at A=490 nm and fx=1.37 $mm^{-1}$.

The sensitivity and accuracy of the SLI system was evaluated with aqueous tissue simulating phantoms, mimicking the expected contrast and background absorption in human breast tissue. Two sets of phantoms were characterized: a first set with variations in particle size scale distribution, and a second set with variations in BVF and TL concentration to alter both absorption and scattering, independently. The recovered values of $\gamma$ and $\mu'_s$ for each particle size scale distribution were determined. The magnitude of $\gamma$ was unique over all wavelengths for each particle size scale distribution, with $\gamma$ exhibiting a linear relationship with wavelength. The magnitude of $\gamma$ decreased with the increasing contribution of the more isotropic 140 mn spheres compared to the more forward scattering IL. Likewise, the spectral slope of $\mu'_s$ also stratified for each particle size scale distribution, with an increasing slope for greater contributions of the 140 nm spheres and a flatter slope for IL. The greatest dynamic range for both $\gamma$ and $\mu'_s$ to changes in particle size scale distribution appear to be towards the shorter wavelengths of light. Error was calculated as Error=100×[recovered-known]/known, and the mean and standard deviation were computed over all phantoms at each wavelength, yielding (10±5.4)% for $\gamma$ and (5.77±6.6)% for $\mu'_s$. As expected, the recovered $\gamma$ spectra cluster together, independent of both IL concentration and background absorption from BVF. Additionally, the magnitude of the $\mu'_s$ values stratify by the various IL concentrations, independent of the BVF. The mean error in recovering $\gamma$ in the presence of various scattering and absorption concentrations was (4.8±3.1)%, while the mean error for $\mu'_s$ was (12±7.4)%. These phantom studies experimentally validated the ability of the multi-spectral. SLI system to accurately recover and quantify sub-diffusive scatter parameters accurately over a broad range of optical properties, which can be expected for surgical tissues in the visible to NIR wavelength bands.

Optical and Micro-CT Co-Registration Accuracy

Co-registration accuracy between the micro-CT imaging space and optical imaging spaces was evaluated and quantified. A phantom with radio-opaque pegs having an optically bright coating was measured with the multimodal system, yielding a micro-CT scan and a co-registered 3D surface mesh of SLI reflectance data. The micro-CT and SLI data were manually thresholded to segment the surface pegs. The co-registration accuracy was quantified for each peg as the Euclidean distance in x, y, z between the centroids of the CT surface and the optical mesh surface. These results showed a mean co-registration accuracy of 620 μm with little variation across the coordinate space. Furthermore, this implies that optical and CT data of breast cancer specimens can be spatially interpreted together within a range 620 μn, or better in later embodiments.

Visualization of a Freshly Resected Breast Tissue Specimen

Evaluation of the histology of a freshly resected breast tissue specimen by a trained pathologist revealed a 2.5 cm lesion of invasive and in situ lobular carcinoma with adjacent, benign fibro-cystic disease (FCD) surround by background adipose. The demodulated intensity was determined at f.=[0, 1.37] $mm^{-1}$ for $\lambda$=490 nm and for $\lambda$=600 nm. For the diffuse images, significantly more contrast occurred between the glandular tissue and adipose for $\lambda$=490 nm compared to the longer wavelengths, due to absorption from β-carotene. However, the superficial high-spatial frequency images at fx–1.37 $mm^{-1}$, revealed similar spatial features for both the shorter and longer wavelengths. Contrast was further quantified over all wavelengths and spatial frequencies. Tumor to adipose had much greater maximum contrast of 5.6 than tumor to FCD, which had a maximum contrast of 1.6, because of the greater dissimilarity in tissue ultrastructure. For both ratios, contrast increased with spatial frequency with the maximum contrast occurring at fx=1.37 $mm^{-1}$, but at $\lambda$=490 ran for tumor to adipose and at $\lambda$=700 um for tumor to FCD. In the axial slice, the tumor mass and spiculations were visible, in the sagittal slice, micro-calcifications appeared as bright specks and the acrylic specimen holder was also visible. Fat and glandular peaks were centered at 0.31 cm-1 and 0.435 cm-1 respectively, and yielded a SNR of 30.1 and contrast of 1.40. While contrast was clearly visible between the glandular tissue and background, negligible contrast occurred within the glandular region between areas of tumor and FCD, unlike the SLT data.

Superficial SLI and volumetric micro-CT data were simultaneously rendered in the open-source Slicer environment.

In embodiments, SLI are also analyzed for color and texture or radiomic features, then used with a classifier and micro-CT data to map tissue type across each specimen.

Clinical Study of 42 Surgical Breast Specimens

Post-surgical breast specimens were obtained from multiple patients.

Specimen imaging occurred postoperatively for this study during standard pathological processing and did not hinder clinical workflow. Each of the resected tumors was "breadloafed" or sliced into ~5-mm sections along the axis perpendicular to the long axis of the lump. One slice from the lump was selected by a pathology specialist and imaged with random anatomical orientation. Image data were therefore assumed to be free of rotational bias. After standard-of-care histological processing and staining with hematoxylin and eosin, a board-certified breast pathologist determined microscopic regions of interests (ROIs) that were manually coregistered to wide-FOV SFDI demodulated image data. For an imaged slice, SFDI ROIs were conservatively outlined within the histopathologic ROIs. ROIs did not necessarily encompass the entirety of each specimen. Many lesions were relatively small compared to the total surface area of the specimens. ROI selection was intentionally conservative to ensure that the lesions were completely contained within the regions.

The enrolled tissue ROIs were sampled to create square subimages of constant size. The sampling process resulted in a subset of the original dataset being considered for texture analysis.

Region of Interest Sampling

Figure 10A:
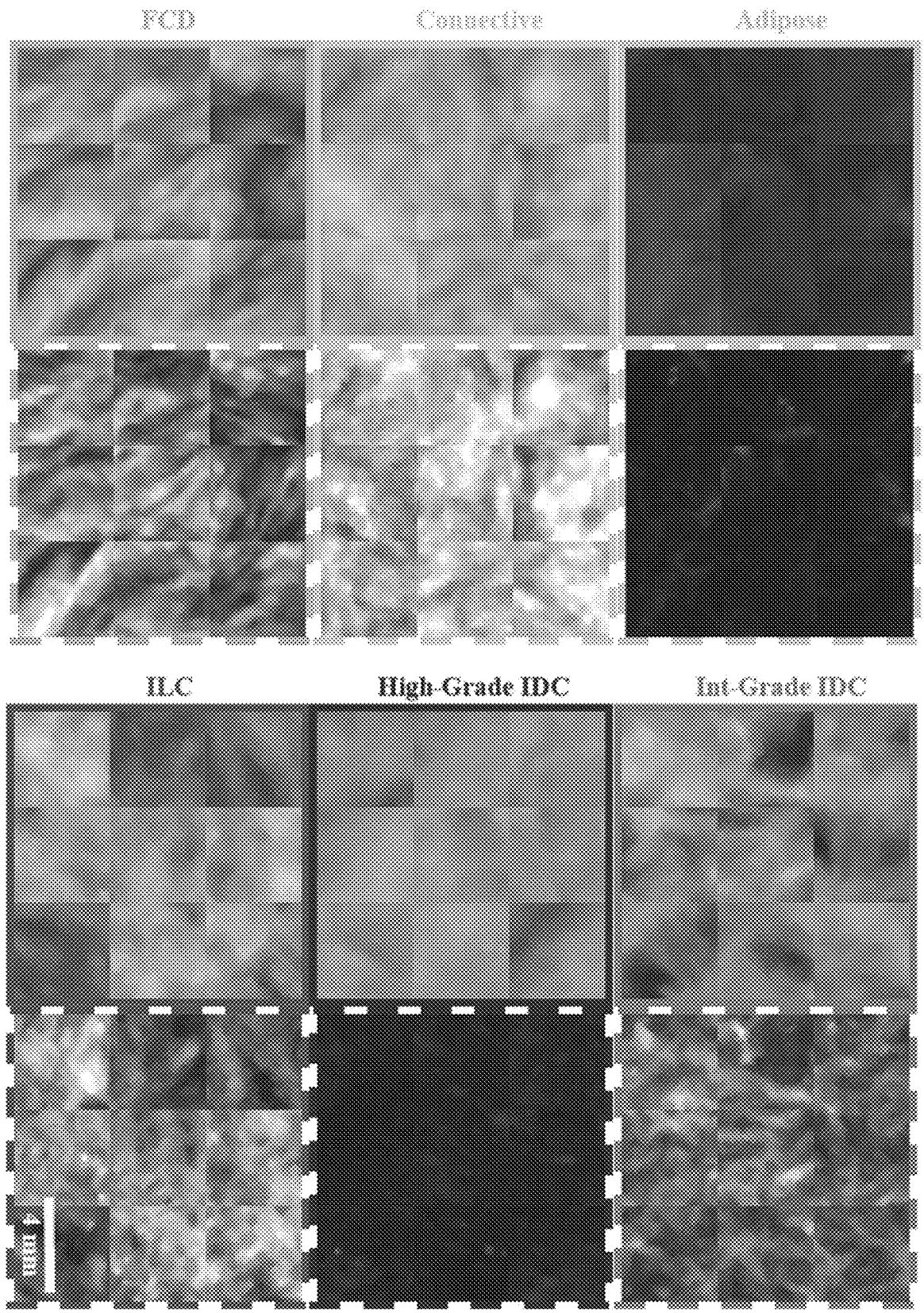
FIG. 10A is an illustration of textures or radiomic features that may be identified and analyzed to determine tissue types as was done in the clinical study of 42 surgical specimens, images surrounded by solid borders are obtained under planar non-spatially-modulated illumination, while images surrounded by dashed borders are obtained under spatially modulated illumination.

Texture analysis was performed on 32×32-pixel (i.e. 4×4 mm$^2$) subimage samples extracted from each specimen ROI. The size was chosen such that macroscale tissue features were captured in each subimage. Square subimage sampling enabled direct comparisons of localized tissue textures found in different tissue subtypes. A custom MATLAB script implemented a simple sliding-box algorithm for subimage sampling. Tissue diagnoses found in fewer than n=3 specimens and ROIs too small to contain a single sample were excluded. Samples with large specular reflections were identified and censured via a custom MATLAB script based on the median absolute deviation of pixel intensities in each sample. A total of 42 specimens containing 56 ROIs (37 benign and 19 malignant) met these criteria. The primary cause for data exclusion was the requirement of a 4×4 mm2 sample of confirmed and homogeneous tissue. Several lesion ROIs in the dataset were too small or irregular in shape to contain a ~4×4 mm$^2$ sample. The 56 eligible ROIs provided a total of 163 subimages (100 benign and 63 malignant) for texture analysis. FIG. 10 summarizes the 163 samples with respect to tissue subtype, specimen (or ROI) count, and sample count.

Benign tissue subtypes considered for texture analysis were adipose tissue, connective tissue, and FCD. Fibroadenoma was not included in the analysis. This type of benign lesion, although present in sufficient numbers for inclusion (4 ROIs and 24 samples), was assumed to be of nominal clinical importance because it is typically known prior to surgery and rarely warrants a re-excision procedure. Malignant subtypes considered for texture analysis were intermediate- and high-grade intra-ductal carcinoma (IDC) and invasive lobular carcinoma (ILC) (i.e., only invasive cancers). Subdiffuse reflectance was found sensitive to small-scale surface tissue features that are occult to typical, planar illumination imaging. We related the various sub-diffuse reflectance textures observed to underlying tissue subtype compositions.

Texture and Radiomic Feature Analysis

Texture analysis of spectroscopic images is known to provide unique information about scattering ultrastructures in human breast tissues. Here, texture is considered an analysis tool for sd-SFDI data. A variety of texture representations were explored in this work, all of which can be broadly categorized as statistical, structural, or transform-based in nature. Texture is considered an analysis tool for both the micro-CT tomography data and the optical data. The optical data analyzed in these experiments was the demodulated data obtained during structured-light imaging. Additional texture and radiomic features may be analyzed in additional embodiments, the detailed description here focuses on analyzing a subset of possible features. These three representations of texture have been used to analyze radiological images of biological tissues, including mammography. Statistical metrics included gray-level co-occurrence matrix (GLCM) contrast, correlation, and homogeneity. Structural or image primitive metrics included fractal dimension, lacunarity, and Euler number. Transform-based metrics were derived from Fourier transform power spectral density (PSD) curve linear fit parameters. Details associated with GLCM pixel statistics, structural image primitives, and Fourier transform PSD curve parameters are given below.

Figure 11:
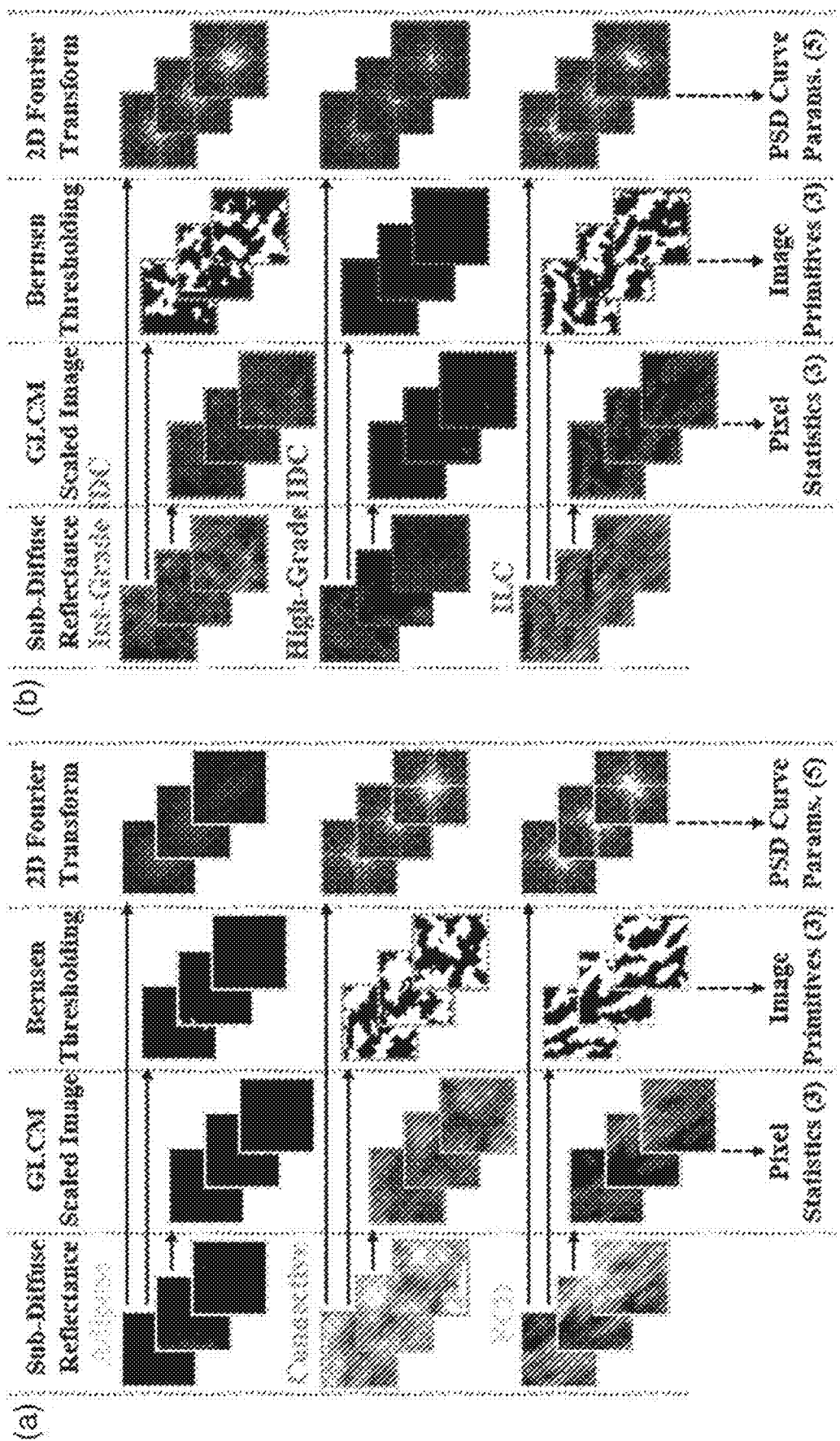
FIG. 11 provides an overview of three representations of texture investigated in the clinical study of 42 surgical specimens giving qualitative comparisons between tissue subtypes within the samples.

Texture analysis generated a total of eleven features associated with each sample. All metrics were quantified rapidly for each sample (<1 s). FIG. 11 provides an overview of the three representations of texture investigated here and gives qualitative comparisons between tissue subtypes undergoing each type of texture analysis.

The Mann-Whitney U-test was used to test the null hypothesis that two samples come from the same population. The Mann-Whitney U-test was chosen to quantify p-values due to small sample sizes and to avoid the assumption of normally distributed metrics. U-test p-values quantified the statistical significance of pixel statistics, image primitives, and PSD curve parameters between the three benign and three malignant tissue subtypes.

Gray-Level Co-Occurrence Matrix Pixel Statistics

The GLCM representation of texture features assesses the spatial dependence of pixel intensities within an image. Pixel statistics of contrast, correlation, and homogeneity were calculated for each sample based on eight-level grayscale intensity images (8×8-element GLCMs). Contrast quantifies the local variation in an image, correlation measures its gray-tone linear dependencies, and homogeneity assesses the prevalence of gray-tone transitions: Each GLCM invoked a one-pixel displacement distance and vector directionality symmetric about 0 deg, 45 deg, 90 deg, and 135 deg. Reported values were averaged over the four angles. Each GLCM was generated using the MATLAB graycomatrix function, and statistics were quantified via the MATLAB graycoprops function.

Image Primitives

The arrangement of repeating patterns or features in an image, referred to as image primitives, were also used to characterize texture. Samples were converted into binary format using a Bernsen local thresholding algorithm implemented in MATLAB. Bemsen thresholding is based on local contrast within a moving window (a 13×13-pixel window here). Local contrast thresholding was found to effectively isolate reflectance structures sometimes lost by global thresholding. Euler number, fractal dimension, and lacunarity were quantified for each binary sample. Euler number codifies the difference between the number of connected components or objects in an image and the number of holes in those objects. Euler number was computed using the MATLAB function bweuler. The Hausdorff box-counting fractal dimension, which is a measure of self-similarity and roughness in an image, was computed using the MATLAB function hausDim. Lacunarity is a measure of inhomogeneity or transitional and rotational invariance of features in an image. Lacunarity was computed by the MATLAB function lacunarity_glbox.

Power Spectral Density (PSD) Curve Parameters

A PSD curve depicts the relative amplitude of spatial frequencies within an image. The PSD curve of each sample was calculated via a two-dimensional (2-D) discrete Fourier transform (DFT) followed by radial averaging of the amplitude of the shifted image data. Radial averaging decomposed the 2-D image into a 1-D profile, which was then converted to power and normalized by its maximum value. Normalized PSD curves were derived using an adapted form of the MATLAB function raPsd2d. Parameterization involved visual identification of two distinct spatial frequency ranges that consistently exhibited different slopes in the PSD curves. These two spatial frequency ranges formed low spatial frequency (LSF) and HSF PSD contributions. Linear fits were applied to these two spatial frequency ranges, yielding slope and intercept parameters for each contribution. The spatial frequency at which the two linear fits intersected provided a fifth parameter.

The LSF and HSF ranges for linear fit parameterization were set to 0 to 1 $mm^{-1}$ and 1 to 2 $mm^{-1}$, respectively. These ranges were selected after inspection of an ensemble of PSD curves for all samples, shown in FIG. 12A. In FIG. 12B, the five linear fit parameters derived from each PSD curve are illustrated. To demonstrate the potential value of PSD curve parameterization, the PSD curves for all adipose tissue and ILC samples tallied in FIG. 10 are plotted together in FIG. 12B Adipose tissue and ILC samples contain significantly different spatial frequency content indicated by different HSF linear fit slopes and intercepts. In contrast, visual inspection of all FCD and ILC PSD curves, plotted together in FIG. 12C shows similar linear fits. The comparison in FIGS. 12B and 12C reinforces the concept that different representations of texture may be effective at distinguishing different types of tissue. The comparison also highlights the fact that when tissues appear different visually, texture-based feature extraction algorithms are likely to discriminate them quantitatively.

Automatic Classification of Tissue Types

In this work, sd-SFDI reflectance texture metrics were provided as input to a machine learning framework for tissue subtype classification. Binary classifications were performed between the three benign and three malignant breast tissue diagnoses. Texture feature vectors associated with one benign tissue subtype and one malignant tissue subtype were classified using a linear SVM classifier (MATLAB function fitcsvm with default settings) with correlation-based feature selection. Classification performance was evaluated using random fivefold cross-validation (CV). Fivefold CV was chosen such that each train/test set contained >30 samples and was representative of the broader dataset. Feature selection used two-sample t-tests (MATLAB function ttest2) across all 11-texture metrics and a grid-search for determining the optimal number of features to include in classification. The grid search involved using a range of features (e.g., one feature, two features, etc.) in the classification model, and the optimal number of features corresponded to the highest classification accuracy achieved. Feature selection identified the most relevant parameters for classification, thereby reducing the dimensionality of the classification problem and mitigating overfitting to noise in the data. Classification used randomized sample size matching, which injected randomness into classification results. Each classification scenario was repeated n=100 times to quantify variability in classification outcomes. Tissue classifications include benign and malignant tissue types.

In alternative embodiments, trainable classifiers including support vector machine (SVM) classifiers, neural network (NN) classifiers, and k-nearest-neighbor (kNN) classifiers may be trained on a large collection of samples that are classified by trained pathologists and used to classify tissue types based upon the micro-CT and sd-SFDI texture data. In addition, rule-based classifiers may be used with an appropriate rule set may be used. We also expect that the classifier may also receive a tumor type classification determined during pre-surgical needle, or open, biopsy to improve classification discrimination between pixel or regions of pixels corresponding to benign and malignant tissue.

Receiver operating characteristic (ROC) curves were generated for every benign—malignant tissue subtype classification. Area under the ROC curve (AUC), sensitivity, specificity, and accuracy were quantified for every classification iteration. To integrate results over all iterations, average ROC curves were generated using a vertical averaging technique, 4' and average performance metrics were derived from the average ROC curves.

Results and Discussion

Tissue Subtype Reflectance

The composition and structure of biological tissues are characterized by refractive index fluctuations on the order of 10's of nm to 10's of μm. The angular probability of scattering is governed by the relative length scale of the wavelength of light and these refractive index fluctuations. Structures on the same length scale or larger than the wavelength of light cause Mie-type scattering, which is forward scatter dominant. Meanwhile, structures that are smaller than the wavelength of light give rise to Rayleigh-type scattering, which is isotropic in nature with relatively more backscattering. Reflectance-based sd-SFDI thus detects lower intensity signals from forward-dominant Mie-type scatterers and higher intensity signals from Rayleigh-type scatterers. By this mechanism, the density, composition, and spatial arrangement of biological structures in surface tissue (<1 mm in depth-2) lead to different subdiffuse reflectance textures.

Adipose tissue is composed primarily of adipocytes, which contain forward-scattering vacuoles with length scales >25 pm. Adipose tissue is characterized by a relatively low intensity, homogeneous subdiffuse reflectance signal. Connective or fibroglandular tissues contain collagen fibers (length scale >1 pm), which are weakly backscattering, and collagen fibrils (length scale of 10s of nm), which act as strong Rayleigh scatterers. Together, these structures create relatively high intensity, structured subdiffuse reflectance. FCD, a common type of benign lesion, can be characterized by fibrosis (i.e., proliferation of connective tissue) of surrounding stroma, resulting in Rayleigh scattering structures on the order of millimeters. As a final example, high-grade IDC is characterized by an elevated density of nuclei (~5 μm in diameter), which are relatively large, forward scattering cellular components. This may explain why high-grade IDC yields a relatively low intensity, homogeneous subdiffuse reflectance comparable to adipose tissue. Comparing adipose tissue and high-grade IDC demonstrates that using sd-SFDI reflectance texture analysis alone may not be effective for surface tissue diagnostics, because different tissue subtypes may contain biologically distinct Mie- or Rayleigh-type scatterers that give rise to similar subdiffuse reflectances. In the case of adipose tissue and high-grade IDC, sd-SFDI texture in combination with tissue color properties (readily discernable from the optical images recorded at the 7 wavelengths used) would overcome this limitation.

In summary, subdiffuse reflectance enhances contrast to small-scale surface tissue texture relative to diffuse, planar illumination imaging.

Texture Metric Statistical Significance

Mann-Whitney U-test p-values were computed between all benign and malignant breast tissue diagnoses using the 11 statistical, structure, and transform-based texture metrics. Metrics across all three representations of texture demonstrated statistically significant differences between the three benign and three malignant tissue subtypes. p-values were quantified using texture metrics derived from all subimages due to the limited number of samples of each tissue subtype. Consequently, p-values are not robust against interpatient bias. This limitation could be overcome in future studies with larger sample sizes.

Gray-Level Co-Occurrence Matrix Pixel Statistics

Subdiffuse reflectance of adipose tissue exhibits low contrast, low correlation, and high homogeneity relative to all malignant diagnoses. These results are expected given that adipose tissue is predominately forward scattering with relatively low intensity, unstructured reflectance. Adipose tissue can be separated from tissue with all three malignant diagnoses with statistical significance using GLCM metrics. Subdiffuse reflectance from connective tissue and FCD exhibits high contrast, high correlation, and low homogeneity relative to all malignant diagnoses. The combination of weakly backscattering collagen fibers and strongly backscattering collagen fibrils in connective tissue and the fibrotic nature of FCD might explain these statistics. Notably, the three GLCM statistics separate FCD from the malignant diagnoses, including ILC. The probability of a breast cancer patient having both FCD and ILC is low. However, the capability of GLCM metrics to statistically separate these two diagnoses is important; we found that optical scatter and color properties alone were unable to statistically separate these two diagnoses.

Image Primitives

The Bernsen local thresholding rendered many of the low intensity, low contrast adipose tissue samples featureless. This explains the low fractal dimension, unit lacunarity, and zero Euler number for this tissue subtype. High-grade IDC samples follow a similar trend but to a lesser extent. The highly structured reflectances characteristic of connective tissue and FCD result in relatively high lacunarity. These results are expected given the rotational variance of these samples. Intermediate-grade IDC and ILC exhibit pock-marked textures that result in elevated Euler numbers. Fractal dimension and lacunarity also statistically separate the rare combination of FCD and ILC.

Power Spectral Density Curve Parameters

Figure 13:
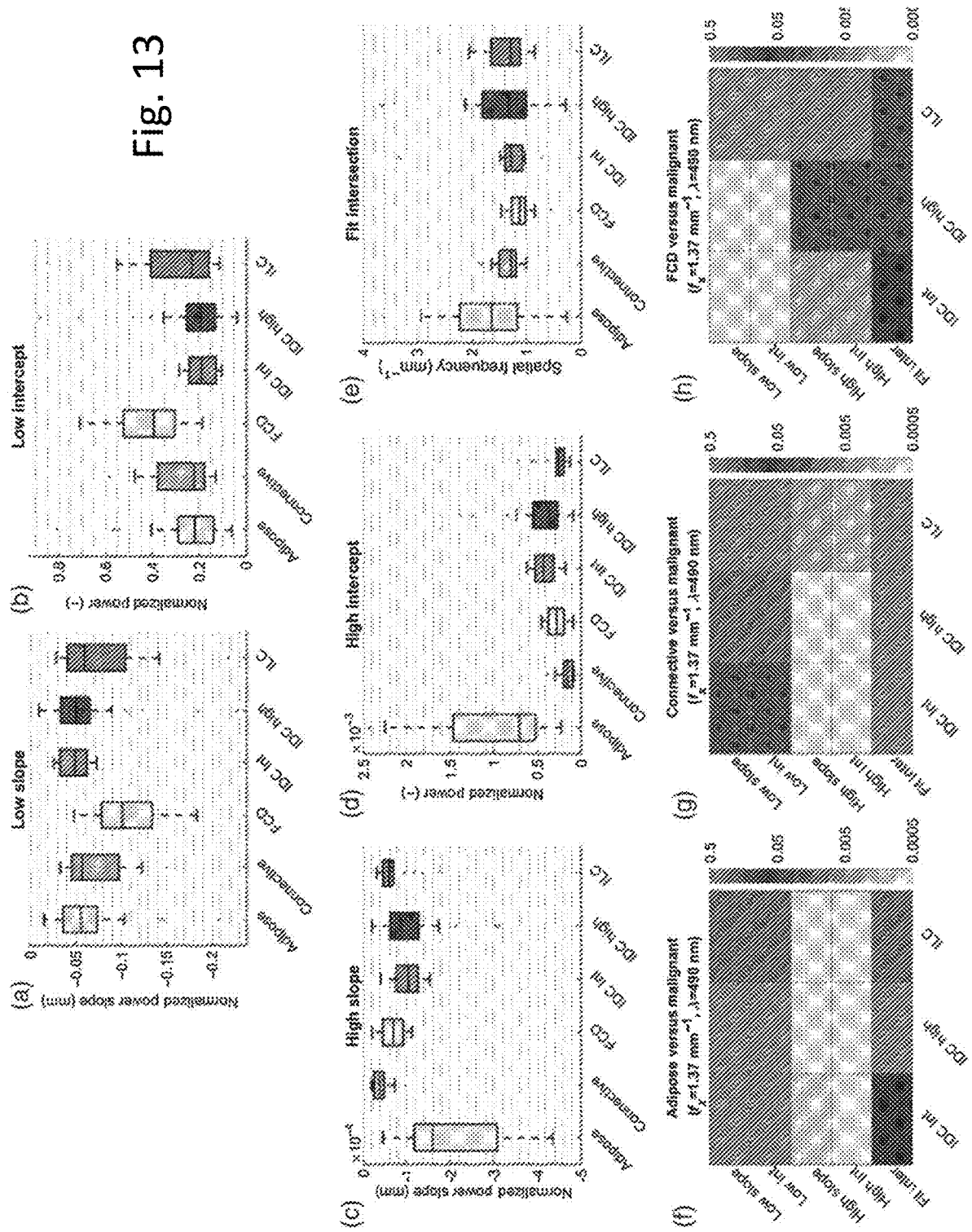
FIG. 13 illustrates boxplots of PSD for various tissue types showing that tissue types can be distinguished on basis of PSD.

FIG. 13 represents PSD curve parameters derived from the subdiffuse reflectance samples. In panel A, FCD samples present with relatively steep LSF slope, indicative of less LSF range content overall. In panel B, LSF slope and intercept are both statistically distinct between FCD and the three malignant tissues. HSF slope and intercept separate both adipose tissue and connective tissue samples from the malignant tissue samples. Adipose tissue presents with a steeper HSF slope, because adipose tissue reflectance contains relatively less HSF range content. Connective tissue samples exhibit a more gradual HSF slope relative to the malignant tissues, because connective tissue reflectance contains additional HSF features relative to the malignant tissues.

Classification Analysis

The ROC curves in FIGS. 14A, 14B, and 14C reflect optimal classification performance based on a feature selection grid search. FIG. 15 summarizes optimal classification performance in the form of AUC, sensitivity, specificity, and accuracy with 95% confidence intervals. Adipose tissue versus intermediate-grade IDC and ILC can be classified with relatively high accuracy compared to adipose tissue versus high-grade IDC. Connective tissue can be classified against high-grade IDC with relatively high accuracy compared to connective tissue versus ILC. FCD can be classified relatively well against high-grade IDC, whereas the model is less effective at classifying FCD versus ILC. Accuracy confidence intervals are wide for some tissue subtypes given the sample sizes.

Figure 17:
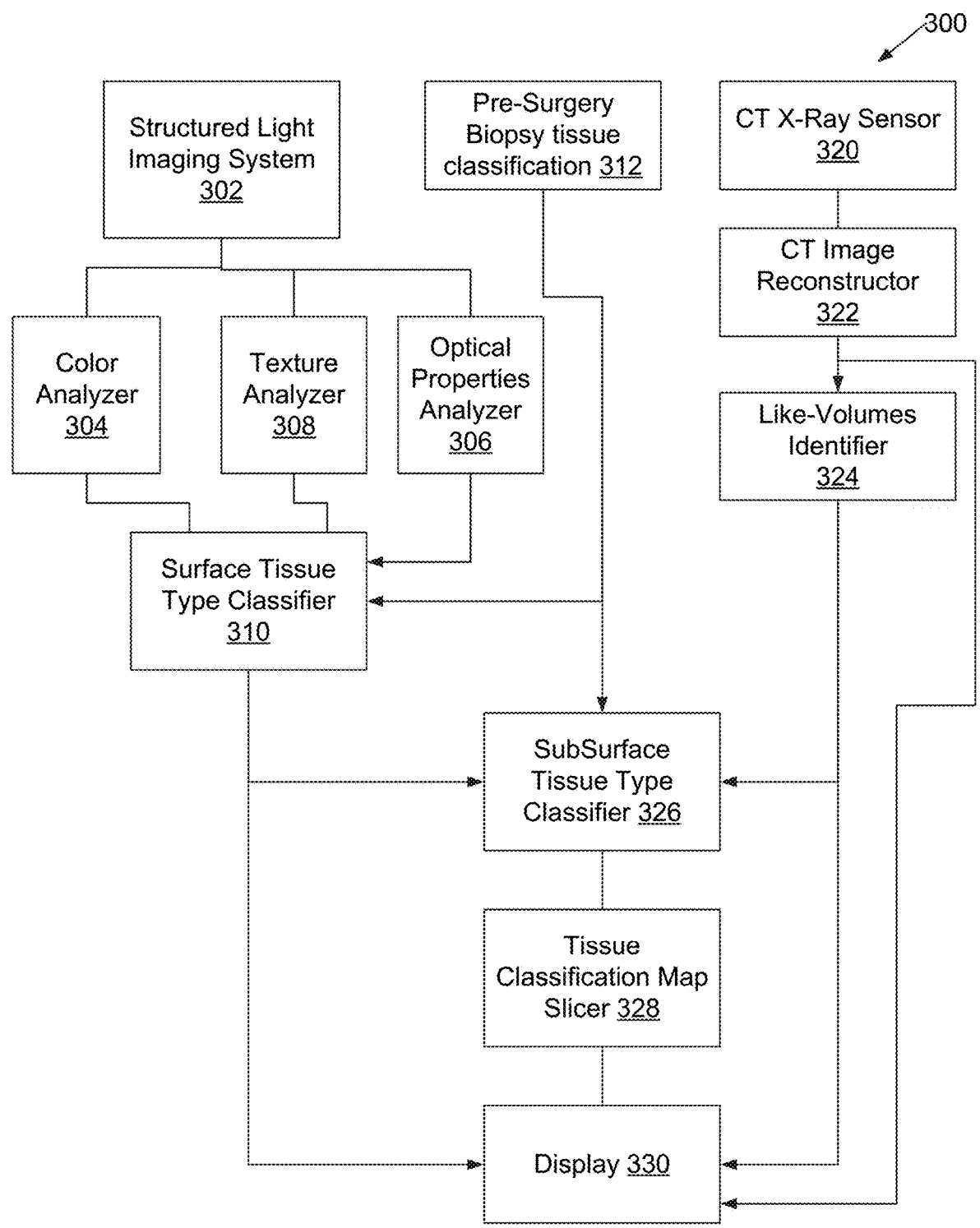
FIG. 17 is a data flow diagram illustrating how the micro-CT and HFT-SLI images are combined and used to classify tissue at surgical boundaries of the specimen.

The texture features used in optimal classifications are reported in FIGS. 16A, 16B, and 16C in heat map form. The most frequently used metrics in benign-malignant classification pairs are boxed in gray, and the percent of the n=100 classifications that employed the given metric is displayed. FIGS. 16A, 16B, and 16C indicates that the most valuable metric for classifying adipose tissue versus intermediate-grade IDC or ILC is GLCM correlation, and classifying adipose versus high-grade IDC involved a more distributed selection of metrics. In FIG. 16B a range of metrics were used to classify connective tissue versus intermediate-grade IDC and ILC. GLCM correlation was always found in the optimal classification of connective tissue versus high-grade IDC. In FIG. 16C, GLCM contrast and correlation were the most important features for classifying FCD against the malignant tissue subtypes. FIG. 17 reports the optimal number of features used in every benign-malignant classification. Values are averaged over all n=100 iterations and rounded to the nearest integer. No classification scenario used more than eight texture features on average. The benign-malignant pair that used the most features for optimal classification was connective tissue versus ILC, which demonstrated the poorest classification performance overall.

FURTHER EMBODIMENTS

The classification model studied used a linear SVM for binary classification, but tissue diagnostics is inherently a multiclass classification problem, potential clinical value would be increased with a multiclass classification model. Classification results reveal that reflectance texture analysis has both strengths and weaknesses. Subdiffuse reflectance is directly related to microscopic structures in tissue but does not necessarily provide unique signals associated with all tissue subtypes diagnosed on the histopathological level. Adipose tissue and high-grade IDC cannot be accurately resolved using subdiffuse reflectance alone using the model presented here. The same applies for differentiating between connective tissue or FCD from ILC. Combining tissue texture features with other tissue properties may overcome these limitations. For instance, quantitative color properties can readily separate adipose tissue and high-grade IDC. Future studies could focus on the collection of a larger hold-out dataset, such that the classification model is trained and tested on a subset of the data and a second subset is reserved purely for assessing classification performance.

The potential benefits of subdiffuse reflectance texture quantification include computational efficiency, and avoiding light transport model assumptions, which may lead to additional errors. Still, it is known that optical properties offer invaluable characterization of a wide range of biological tissues. Future work should compare surface tissue classification performance using sd-SFDI reflectance textures and optical properties and combinations of the two. In summary, additional studies are required to validate these classification results on even larger sample sizes, to test the inclusion of other tissue properties in the classification model, including color and pre-surgery biopsy results, and to improve the generalization and applicability of the techniques here disclosed.

SLI and micro-CT are likely to be complementary, as the micro-CT lacks contrast between benign and malignant glandular tissues hut provides a 3D reconstruction of the tumor core within a specimen, whereas SLI offers enhanced superficial contrast between more subtle morphological changes. Sensitivity to the surface of tissue is substantiated by a current consensus report which states that 'no tumor on ink' is appropriate for early stage invasive breast cancer (Buchholz et al 2014). With this work flow, the micro-CT could guide selection of surfaces to be optically imaged and provide the proximity of suspicious lesions to the tumor mass. Additionally, contextualizing SLI measurements with the subsurface proximity of the tumor-core, as calculated from the micro-CT, could aid in interpretation of the multimodal data.

Combining Modalities

FIG. 17 illustrates data flow 300 including how data from the micro-CT and HFT-SLI results, and the texture-analyzed reflectance images are combined and used to classify tissue at surgical boundaries of the specimen. Raw optical images of the specimen are obtained 302 by the camera 112 (FIG. 1) of the structured-light imaging system. These raw images pass into the image processor 114 where firmware 118 includes firmware to execute a color analyzer 304, texture analyzer 306, and optical properties analyzer 308. Imaging is conducted in unstructured light as well as in structured light as previously described; structured light images are demodulated as previously described.

Color analyzer 304 uses reflectance at each of the seven wavelengths at which imaging is conducted to generate red-green-blue (RGB) human-readable color images and to prepare a hyperspectral color map of the specimen; the color map of the specimen is analyzed for clues to tissue type producing a color features map of the specimen.

Texture analyzer 306 in firmware 118 analyzes texture of surface of the specimen from the demodulated images and as previously described to determine a texture feature map of surface of the specimen, while optical properties analyzer 308 in firmware determines a HFT-SLI optical properties map of the specimen. Texture analyzer 306 operates on both unstructured light and structured light images of the specimen surface, since structured light texture bears important clues to tissue type.

A tissue type of any known abnormal tissue of the patient, such as a cancer type as found by pre-surgical biopsy, is input 312 to the system as it is useful in determining what malignant tissue may look like in the specimen.

The tissue type of any known abnormal tissue, color features map, HFT-SLI optical properties map, and texture features map are all input to tissue type classifier 310, as previously described tissue type classifier is a machine-learning-based classifier. Classifier 310 then provides a tissue-type map of the tissue surface.

Meanwhile, micro-CT scanning is performed with data 320 from the X-ray sensor 106 used by an image reconstruction routine 322 as known in the art of CT scanners to prepare three-dimensional (3D) images of the specimen. These 3D images are used by a like-volumes identifier 324 to recognize volumes of multiple voxels having similar texture and density and thus likely of a same tissue time in the 3D images and to generate a volume map. The 3D images and volume map are input to a sub-surface tissue-type classifier 326 along with the surface tissue-type map from classifier 310, sub-surface tissue-type classifier 326 generates a three-dimensional (3D) tissue-type classification map giving a tissue type for each voxel of the 3D images of the tissue. The 3D tissue-type classification map is then sliced for tomographic imaging by tissue-type map slicer 328 and slices are presented for display 330. Display 330 may also display 3D images from the CT reconstructor 322, like volumes maps from like-volumes identifier 324, and surface tissue-type maps from tissue-type classifier 310.

In embodiments, sub-surface tissue-type classifier 326 is also a machine-learning-based classifier such as a kNN classifier, neural network classifier, or SVM classifier. The 3D tissue-type map and the tissue-type map of the surface both distinguish between likely malignant tissue from benign tissues and these maps are provided to a surgeon who may remove additional tissue from the patient from whom the surgical specimen was taken, the addition tissue to be removed being adjacent to where malignant tissue is shown in the surgical specimen as being close to or at the surface of the surgical specimen.

In embodiments, surgery is performed by anesthetizing a patient having malignant tissue, removing a surgical specimen containing malignant tissue from the patient, analyzing the surgical specimen as herein described to generate a tissue type map of the surgical specimen, and inspecting the tissue type map to determine if surgical margins are adequate. Based upon the tissue type map, the surgeon determines whether and how much additional tissue should be removed from the patient prior to closing the surgical wound.

Changes may be made in the above system, methods or device without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. A system for specimen imaging with combined x-ray and optical measurement comprising:
   a micro-X-ray computed tomography (CT) unit configured to provide voxel-based CT images of the specimen;
   a structured light imaging (SLI) unit configured to provide optical images obtained at a plurality of wavelengths, a plurality of structured light phases, and at a plurality of structured-light pattern periods;
   an image processing unit configured to receive the CT images and the optical images and configured by firmware in memory to:
   demodulate the structured light images;
   register the CT and optical images;
   extract like-tissue volumes from the CT images to form a volume map;
   process the optical images to determine texture at a plurality of subimages of the optical images, the determined textures forming a texture map;
   use a first machine-learning-based classifier to determine a surface tissue type map of the specimen from the texture map; and
   use a second machine-learning-based classifier to determine a three-dimensional tissue-type map from the surface tissue type map and the extracted like-tissue volumes from the CT images.

2. The system of claim 1 wherein the first and second machine-learning-based classifiers are each selected from the group consisting of support vector machine classifiers, neural network classifiers, and k-nearest-neighbor classifiers.

3. The system of claim 2 where the surface tissue type map distinguishes malignant from benign tissue in the specimen.

4. The system of claim 3 where the image processing unit is further configured to process the optical images to determine optical properties at a plurality of pixels, thereby forming optical-properties images, and where the machine-learning-based classifier uses the optical-properties images in forming the tissue type map.

5. The system of claim 4 where at least one of the structured light periods is 1.37 mm$^{-1}$.

6. The system of claim 5 where the structured light phases comprise at least three phase offsets.

7. The system of claim 1 where the firmware further comprises firmware to perform color analysis on the optical images to form a color map, and where the first machine-learning-based classifier is configured to use the color map in producing the surface tissue type map.

8. The system of claim 7 where the tissue-type map includes a map of malignant versus benign tissue.

9. A method of analyzing surgical specimens comprising:
   illuminating a surgical specimen with structured light from a structured-light illuminator;
   imaging the surgical specimen to provide optical images at a plurality of illumination wavelengths, a plurality of structured light phases, and a plurality of structured-light pattern periods;
   demodulating the optical images;
   processing the optical images to determine texture at a plurality of subimages of the optical images, the determined textures forming a texture map; and
   classifying with a first machine-learning-based classifier to determine a surface tissue type map of the specimen from the texture map;
   obtaining X-ray computed tomography (CT) images of the surgical specimen;
   registering the CT and optical images;
   extracting like-tissue volumes from the CT images to form a volume map; and
   classifying with a second machine-learning-based classifier to determine a three-dimensional tissue-type map from the surface tissue type map and the extracted like-tissue volumes from the CT images.

10. The method of claim 9 further comprising performing color analysis on the optical images to form a color map, and where the first machine-learning-based classifier is configured to use the color map in producing the surface tissue type map.

11. The method of claim 10 wherein the first and second machine-learning-based classifiers are each selected from the group consisting of support vector machine classifiers, neural network classifiers, and k-nearest-neighbor classifiers.

12. The method of claim 10 further comprising processing the optical images to determine optical properties at a plurality of pixels, thereby forming optical-properties images, and where the machine-learning-based classifier uses the optical-properties images in forming the tissue type map.

13. A method of performing surgery comprising the method of claim 9 and further comprising performing surgery to remove a cancerous lesion from a patient to provide the surgical specimen, and using the tissue type map to determine whether and how much additional tissue should be removed from the patient prior to ending the surgery.

* * * * *